(12) United States Patent
Gunawardhana et al.

(10) Patent No.: US 9,107,912 B2
(45) Date of Patent: *Aug. 18, 2015

(54) METHODS FOR CONCOMITANT TREATMENT OF THEOPHYLLINE AND FEBUXOSTAT

(75) Inventors: Lhanoo Gunawardhana, Pleasant Prairie, WI (US); Max Tsai, Highland Park, IL (US); Himanshu Naik, Evanston, IL (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/227,828

(22) Filed: Sep. 8, 2011

(65) Prior Publication Data

US 2012/0065236 A1 Mar. 15, 2012

Related U.S. Application Data

(60) Provisional application No. 61/381,482, filed on Sep. 10, 2010.

(51) Int. Cl.
*A61K 31/522* (2006.01)
*A61K 31/426* (2006.01)
*A61K 31/415* (2006.01)
*A61K 45/06* (2006.01)

(52) U.S. Cl.
CPC ............ *A61K 31/426* (2013.01); *A61K 31/415* (2013.01); *A61K 31/522* (2013.01); *A61K 45/06* (2013.01)

(58) Field of Classification Search
CPC . A61K 31/426; A61K 31/415; A61K 31/522; A61K 45/06
USPC ............................................ 514/365, 263.34
See application file for complete search history.

(56) References Cited

U.S. PATENT DOCUMENTS

| 3,079,303 | A | 2/1963 | Raff et al. |
| 4,058,614 | A | 11/1977 | Baldwin |
| 4,156,732 | A | 5/1979 | Lang |
| 4,296,122 | A | 10/1981 | Cragoe |
| 4,510,322 | A | 4/1985 | Blaine |
| 4,632,930 | A | 12/1986 | Carini et al. |
| 5,047,246 | A | 9/1991 | Gallian et al. |
| 5,268,386 | A | 12/1993 | Harada et al. |
| 5,358,961 | A | 10/1994 | Lee et al. |
| 5,514,681 | A | 5/1996 | Wren |
| 5,614,520 | A | 3/1997 | Kondo et al. |
| 5,693,818 | A | 12/1997 | Von Unge |
| 5,770,601 | A | 6/1998 | Wren |
| 5,883,137 | A | 3/1999 | King |
| 5,965,625 | A | 10/1999 | King |
| 6,015,829 | A | 1/2000 | Ishibuchi et al. |
| 6,037,344 | A | 3/2000 | Wren |
| 6,225,474 | B1 | 5/2001 | Matsumoto et al. |
| 6,281,222 | B1 | 8/2001 | Salzman et al. |
| 6,569,862 | B1 | 5/2003 | Marban |
| 7,074,816 | B2 | 7/2006 | Nakamura et al. |
| 7,361,676 | B2 | 4/2008 | Iwai et al. |
| 8,372,872 | B2 * | 2/2013 | Gunawardhana et al. ..... 514/365 |
| 2002/0019360 | A1 | 2/2002 | Kivlighn |
| 2002/0187120 | A1 | 12/2002 | Holmes-Farley et al. |
| 2003/0039627 | A1 | 2/2003 | Holmes-Farley et al. |
| 2003/0186998 | A1 | 10/2003 | Marban |
| 2004/0121004 | A1 | 6/2004 | Taneja |
| 2004/0122067 | A1 | 6/2004 | Zhao |
| 2004/0131676 | A1 | 7/2004 | Taneja |
| 2005/0070552 | A1 | 3/2005 | Fedida et al. |
| 2006/0040945 | A1 | 2/2006 | Smolka et al. |
| 2006/0252808 | A1 | 11/2006 | Joseph-Ridge |
| 2007/0167454 | A1 | 7/2007 | Lademacher |
| 2008/0269226 | A1 | 10/2008 | Lademacher |
| 2009/0042887 | A1 | 2/2009 | Lademacher et al. |
| 2009/0124623 | A1 | 5/2009 | Lademacher et al. |
| 2010/0311756 | A1 | 12/2010 | Zhao |
| 2012/0065207 | A1 | 3/2012 | Gunawardhana |
| 2012/0065215 | A1 | 3/2012 | Gunawardhana |
| 2013/0143886 | A1 | 6/2013 | Lademacher et al. |

FOREIGN PATENT DOCUMENTS

| DE | 2707268 | 8/1978 |
| DE | 2707269 | 8/1978 |
| DE | 2707270 | 8/1978 |
| DE | 3112116 | 11/1982 |

(Continued)

OTHER PUBLICATIONS

Ernst et al. Febuxostat: A selective xanthine-oxidase/xanthine-dehydrogenase inhbitor for the management of hyperuricemia in adults with gout. Clinical Therapeutics/vol. 31, No. 11, 2009 pp. 2503-2518.*
United States Patent Office Action for U.S. Appl. No. 12/210,207 dated Jul. 31, 2012 (18 pages).
Allopurinol Drugdex Drug Evaluations, Thompson Micromedix, 2006, 52 pages.
Antiplatelet Trialists Collaboration et al., Collaborative overview of randomised trials of antiplatelet therapy- I Prevention of death, myocardial infarction, and stoke by prolonged antiplatelet therapy in various categories of patients, BMJ vol. 308, pp. 81-106, Jan. 8, 1994.
Anzai et al., Renal Urate Handling: Clinical Relevance of Recent Advances, Current Science Inc. Copyright 2005, pp. 227-234.
Arakawa et al., Allopurinol Hypersensitivity Syndrome Associate with Systemic Cytomegalovirus Infection and Systemic Bacteremia, International Medicine vol. 40, No. 4, pp. 331-335 (Apr. 2001).
Arellano et al., Allopurinol Hypersensitivity Syndrome—A Review, The Annals of Pharmacotherapy, vol. 27, pp. 337-341, Mar. 1993.

(Continued)

*Primary Examiner* — Jennifer M Kim
(74) *Attorney, Agent, or Firm* — Lisa V. Mueller; Michael Best & Friedrich LLP

(57) ABSTRACT

The present disclosure relates to a method of treating hyperuricemia in a patient that also suffers from a second disease state requiring treatment with theophylline, wherein the patient receives concomitant treatment with a xanthine oxidoreductase inhibitor and theophylline without resulting in theophylline toxicity to the patient and without substantial adjustments to the manufacturer's recommended dosage of theophylline.

6 Claims, 1 Drawing Sheet

(56) References Cited

FOREIGN PATENT DOCUMENTS

| | | |
|---|---|---|
| EC | SP99-3280 | 12/1999 |
| EP | 0000128 | 1/1979 |
| EP | 0104483 | 4/1984 |
| EP | 0415566 | 6/1991 |
| EP | 0779074 | 6/1997 |
| EP | 0936217 | 8/1999 |
| GB | 2031882 | 4/1980 |
| JP | 06-345724 | 12/1994 |
| JP | 7-242694 | 9/1995 |
| JP | 10-045773 | 2/1998 |
| JP | 11-140086 | 5/1999 |
| JP | 2002105067 | 4/2002 |
| WO | WO 92/09279 | 6/1992 |
| WO | WO 93/04688 | 3/1993 |
| WO | WO 96/26208 | 8/1996 |
| WO | WO 99/24038 | 5/1999 |
| WO | WO 00/07193 | 2/2000 |
| WO | WO 00/07629 | 2/2000 |
| WO | WO 00/27394 | 5/2000 |
| WO | 00/35424 | 6/2000 |
| WO | WO 01/012204 | 2/2001 |
| WO | WO 02/00210 | 1/2002 |
| WO | 02/062330 | 8/2002 |
| WO | WO 03/037332 | 5/2003 |
| WO | WO 03/064410 | 8/2003 |
| WO | WO 2004/009563 | 1/2004 |
| WO | WO 2006/028342 | 3/2006 |
| WO | WO 2006/055412 | 5/2006 |
| WO | WO 2007/019153 | 2/2007 |
| WO | 2007/062028 | 5/2007 |
| WO | WO 2008/089296 | 7/2008 |
| WO | WO 2009/041798 | 4/2009 |
| WO | WO 2010/030988 | 3/2010 |
| WO | 2011/162390 | 12/2011 |
| WO | 2012/005365 | 1/2012 |

OTHER PUBLICATIONS

Arromdee et al., Epidemiology of Gout—Is the Incidence Rising, the Journal of Rheumatology 2002; 29:11, pp. 2403-2406.
Baker et al., Serum uric acid and cardiovascular disease: Recent Development, and where do they leave us? The American Journal of Medicine, vol. 118 No. 8, pp. 816-826, Aug. 2005.
Becker et al., Clinical Aspects of Monosodium Urate Monohydrate Crystal Deposition Disease (Gout). Rheumatic Disease Clinics of North America—vol. 14, No. 2, pp. 377-395, Aug. 1988.
Becker et al., We can make Gout Management more successful now, Current Opinion in Rheumatology, vol. 20, pp. 167-172, 2008.
Becker, M. et al., "A Phase 3 Randomized, Controlled, Multicenter, Double-Blind Trial (RCT) Comparing Efficacy and Safety of Daily Febuxostat (FEB) and Allopurinol (ALLO) in Subjects with Gout" [abstract], Amer College Rheum. (2008) Abstract No. L11.
Becker, M.A. et al., A phase 3 study comparing the safety and efficacy of oral febuxostat and allopurinol in subjects with hyperuricemia and gout [abstract]. Arthritis Rheum. Dec. 2004; 50(12):4103-4104. Abstract No. L18.
Becker, M.A. et al., "A safety and efficacy clinical trial of a novel non-purine selective inhibitor of xanthine oxidase, febuxostat in subjects with gout" [abstract]. Ann Rheum Dis. Jul. 2004; 63(Suppl 1):60. Abstract No. OP0007.
Becker, M.A. et al., "Allopurinol intolerant patients treated with febuxostat for 4 years" [abstract]. Arthritis Rheum. Sep. 2006; 54(9 Suppl):S646-S647. Abstract No. 1605.
Becker MA et al., Clinical efficacy and safety of successful long-term urate lowering with febuxostat or allopurinol in subjects with gout. J Rheumatol. (2009) 36(6):1273-1282.
Becker, M.A. et al., Determinants of the clinical outcomes of gout during the first year of urate-lowering therapy. Nucleosides Nucleotides and Nucleic Acids. Jun. 2008; 27(6):585-591.
Becker, M.A. et al., Febuxostat (TMX-67), a novel, non-purine, selective inhibitor of xanthine oxidase, is safe and decreases serum urate in healthy volunteers. Nucleosides Nucleotides Nucleic Acids. Oct. 2004; 23(8 & 9):1111-1116.
Becker MA et al., Febuxostat compared with allopurinol in patients with hyperuricemia and gout, N Engl J Med. Dec. 2005;353(23):2450-2461.
Becker, M.A. et al., "Febuxostat vs allopurinol controlled trial in subjects with hyperuricemia and gout (FACT): a multicenter, phase 3, randomized, controlled, double-blind clinical study" [abstract]. Pharmacotherapy Oct. 2005; 25(10):1488. Abstract No. 359E.
Becker MA et al., Febuxostat, a novel non-purine selective inhibitor of xanthine oxidase, therapy in allopurinol intolerant patients [abstract]. Arthritis Rheum. Sep. 2004;50(9 Suppl):S336. Abstract No. 803.
Becker, M.A. et al., "Febuxostat, a novel nonpurine selective inhibitor of xanthine oxidase, therapy in allopurinol intolerant patients" [abstract]. J Natl Med Assoc. Jun. 2005; 97(6):894.
Becker MA et al., Febuxostat, a novel nonpurine selective inhibitor of xanthine oxidase: a twenty-eight-day, multicenter, phase II, randomized, double-blind, placebo-controlled, dose-response clinical trial examining safety and efficacy in patients with gout. Arthritis Rheum. Mar. 2005;52(3):916-923.
Becker MA et al., Gout flare incidence in relation to average serum urate during the first year of urate-lowering therapy [abstract]. Arthritis Rheum. Sep. 2007;56 (9 Suppl):S322-S323. Abstract No. 758.
Becker MA et al., Long-term urate-lowering therapy in subjects with gout—the EXCEL study [abstract]. International Journal of Rheumatic Diseases. 2008;11 (Suppl 1):A209. Abstract No. P1Q-07.
Becker MA et al., Magnetic resonance imaging (MRI) in the quantitative assessment of gouty tophi [abstract]. Arthritis Rheum. Sep. 2003;48(9 Suppl):S528. Abstract No. 1344.
Becker, M.A. et al., "Magnetic resonance imaging of gouty tophi during treatment with febuxostat, a nonpurine selective inhibitor of xanthine oxidase" [abstract]. J Natl Med Assoc. Jun. 2005; 97(6):883.
Becker MA et al., Reduction in gout flares in subjects with chronic gout treated with febuxostat or allopurinol for 52-weeks: FACT trial [abstract]. Arthritis Rheum. Sep. 2005;52(9 Suppl):S108. Abstract No. 202.
Becker, M.A. et al., "The long-term clinical benefits of febuxostat vs allopurinol in subjects with gout: interim analysis of the EXCEL trial, an ongoing phase 3, open-label extension study" [abstract]. Ann Rheum Dis. Jul. 2006; 65(Suppl 2):431. Abstract No. FRI0484.
Becker MA et al., Urate-lowering pharmacotherapy with febuxostat (FEB) or allopurinol (ALLO) in African-American subjects with gout [abstract]. Arthritis Rheum. Sep. 2007;56(9 Suppl):S637. Abstract No. 1622.
Becker, M.A. et al., "Urate-lowering pharmacotherapy with febuxostat or allopurinol in black-american subjects with gout" [abstract]. Ann Rheum Dis. Jul. 2007; 66(Suppl II):231. Abstract No. THU0340.
Becker, M.A. et al., "Urate-lowering therapy (Febuxostat [FEB] or Allopurinal [ALLO]) in subjects with gout: interim results from the febuxostat comparative extension long-term study (EXCEL)" [abstract]. Ann Rheum Dis. Jul. 2007; 66(Suppl II):230-231. Abstract No. THU0339(757).
Beers, M.H. et al. "221 / Urinary Calculi," The Merck Manual of Diagnosis and Therapy, (1999) pp. 1838-1840.
Beers, M.H. et al. "55 / Crystal-Induced Conditions," The Merck Manual of Diagnosis and Therapy, (1999) pp. 460-464.
Berge et al., "Pharmaceutical salts," J. Pharm. Sci. (1977) 66:1-19.
Berry, C.E. et al., "Xanthine oxidoreductase and cardiovascular disease: molecular mechanisms and pathophysiological implications", J Physiol (2004), 555.3:589-606.
BOF-4272, Drug Print Report, Printed from Website http://release2. id.../report.print_disply?i_query_id=1214721 &template=DrugPrint&id=852, Jan. 17, 2003.
Borstad et al., Colchicine for Prophylaxis of Acute Flares When Initiating Allopurinol for Chronic Gouty Arthritis, The Journal of Rheumatology 2004, 31:12, pp. 2429-2432.
Braunwald, Biomarkers in Heart Failure, N Eng J Med 358;20, pp. 2148-2148 www.nejm.org May 15, 2008, Downloaded from www. nejm.org at Abbott on May 21 2008. Copyright 2008 Massachusetts Medical Society.
Burrell, L.M. "A Risk-Benefit Assessment of Losartan Potassium in the Treatment of Hypertension," Drug Safety (1997) 16(1):56-65.

(56) References Cited

OTHER PUBLICATIONS

Carter, J.D. et al., An analysis of MRI and ultrasound imaging in patients with gout who have normal plain radiographs, Rheumatology vol. 48, pp. 1442-1446, Sep. 10, 2009.
Chao et al., Hypersensitivity Syndrome and Pure Red Cell Aplasia Following Allopurinol Therapy in Patent with Chronic Kidney Disease, The Annals of Pharmacotherapy, vol. 39, pp. 1552-1556, Sep. 2005.
Chen et al., Diagnosis and Management of Gout, JCOM, vol. 10 No. 6, pp. 336-343, Jun. 2003.
Chobanian, A.V. et al., The Seventh Report of the Joint National Committee on Prevention, Detection, Evaluation, and Treatment of High Blood Pressure, U.S. Department of Health and Human Services, NIH Publication No. 04-5230, Aug. 2004, JAMA (2003) 289(19):2560-2572.
Choi et al., Independent Impact of Gout on Mortality and Risk for Coronary Heart Disea0se,America Heart association, Journal of the American Heart Association, vol. 116, pp. 894-900, Aug. 13, 2007.
Choi, Epidemiology of Crystal Arthropathy, Rheumatic Disease Clinic of North America, vol. 32, pp. 255-273, (2006).
Chonchol et al., Relationship of Uric Acid with Progression of Kidney Disease, American Journal of Kidney Diseases, vol. 50, No. 2, pp. 239-247, Aug. 2007.
Cingolani et al., J. Cardiac Failure (2006) 12(7):491-498.
Cirillo et al., Uric Acid, the Metabolic Syndrome, and Renal Disease, Journal of the American Society of Nephrology, vol. 17, pp. S165-S168, 2006.
Cockcroft et al., Prediction of Creatinine Clearance from Serum Creatinine, Nephron, vol. 16, pp. 31-41, 1976.
Cooper, N. et al., "Quantification of uric acid, xanthine and hypoxanthine in human serum by HPLC for pharmacodynamic studies." J Chromatogr B, (2006); 837:1-10.
Daghini, E. et al., Acute inhibition of the endogenous xanthine oxidase improves renal hemodynamics in hypercholesterolemic pigs. Am. J. Physiol. Regul. Integr. Comp. Physiol., Mar. 2006, vol. 290, pp. R609-R615.
Dalbeth at al., Computed Tomography Measurement of Tophus, Arthritis & Rheumatism (Arthritis Care and Research), vol. 57, No. 3, pp. 461-465, Apr. 15, 2007.
Dalbeth et al., Dose Adjustment of Allopurinol According to Creatinine Clearance Does Not Provide Adequate Control of Hyperuricemia in Patients with Gout, The Journal of Rheumatology, 33:8, pp. 1646-1649, 2006.
Day et al., Allopurinol dosage selection: relationship between dose and plasma oxipurinol and urate concentrations and urinary urate excretion, Br. J. Clin Pharmac: pp. 423-428, 1988.
Delorme, N. et al., "Interaction of allopurinol and theophylline," Pharm. Clin. Therapeutique (1987) 26(6):403-404.
Drug and Therapeutics Bulletin, "Gout in Primary Care," (2004) BNF10.1.1 & 10.1.4, p. 37-40.
Elenbaas, R.M. et al., "Prediction of serum theophylline levels," Annals Emergency Medicine (1984) 13(2):92-96 (Abstract).
Emmerson, Drug Therapy—The Management of Gout, The New England Journal of Medicine, vol. 334 No. 7, pp. 445-451, Fe. 15, 1996.
Engberding et al., Circulation (2004) 110:2175-2179.
Fam et al., Desensitization to Allopurinol in Patients with Gout and Cutaneous Reactions, The American Journal of Medicine, vol. 93, pp. 299-301, Sep. 1992.
Fam et al., Efficacy and Safety of Desensitization to Allpourinol Following Cutaneous Reactions, Arthritis & Rheumatism, vol. 44, No. 1, pp. 231-238, Jan. 2001.
Fam, Alternate Urate-Lowering Drugs and the Management of Hyperuricemia in Allopurinol-Intolerant Patients, International Journal of Advances in Rheumatology, vol. 1 No. 4, pp. 122-130, 2003.
FAM, Difficult Gout and New Approaches for Control of Hyperuricemia in the Allopurinol-Allergic Patient, Sunnybrook and Women's College Health Science Center, 3:29-35, 2001.

Fang et al, Serum Uric Acid and Cardiovascular Mortality, The NHANES I Epidemiology Follow-Up Study, 1971-1992, JAMA, vol. 283 No. 18, pp. 2404-2410, May 10, 2000.
Feig et al., Serum Uric Acid—A Risk Factor and a Target for Treatment?, J Am Soc Nephrol, vol. 17, pp. S69-S73, 2006.
Fukunari, A. et al., "Y-700 [1-[3-Cyano-4-(2,2-dimethylpropoxy)phenyl]-1$H$-pyrazole-4-carboxylic Acid]: A Potent Xanthine Oxidoreductase Inhibitor with Hepatic Excretion," The Journal of Pharmacology and Experimental Therapeutics, (2004) 311(2):519-528.
Fyfe et al., Kinetic Properties and Inhibition of Ortidine 5'-Phosphate Decarboxylase, The Journal of Biological Chemistry, vol. 248, No. 11, pp. 3801-3809, 1973.
Garbe et al., Exposure to Allopurinol and the Risk of Cataract Extraction in Elderly Patients, Arch Ophthalmol, vol. 116, pp. 1652-1656, Dec. 1998.
Gibson et al., Renal Impairment and Gout, Annals of Rheumatic Diseases, 39, pp. 417-423, 1980.
Gibson, T. et al., "Tienilic Acid in the Treatment of Gout and Hypertension," Purine Metabolism in Man-III, vol. 122A (1980) 277-282.
Grabowski B et al., Effect of hydrochlorothiazide on pharmacokinetics and pharmacodynamics of febuxostat [abstract]. Arthritis Rheum. Sep. 2005;52(9 Suppl):S103-S104. Abstract No. 190.
Grabowski, B. et al., Pharmacokinetics, pharmacodynamics, and safety of febuxostat (TMX-67), a non-purine selective inhibitor of xanthine oxidase, in healthy subjects [abstract]. J Clin Pharmacol. Oct. 2004; 44(10):1196. Abstract No. 47.
Grabowski, B. A. et al., "Metabolism and Excretion of [$^{14}$C] Febuxostat, a Novel Nonpurine Selective Inhibitor of Xanthine Oxidase, in Healthy Male Subjects." J Clin Pharmacol (2010) 51(2):189-201.
Graessler et al., Association of the Human Urate Transporter 1 with Reduced Renal Uric Acid Excretion and Hyperuricemia in a German Caucasian Population, Arthritis @ Rheumatism, vol. 54, No. 1, pp. 292-300, Jan. 2006.
Gutierrez-Macias et al., Fatal Allopurinol Hypersensitivity syndrome after treatment of asymptomatic hyperuricemia, BMJ vol. 331, pp. 623-624, Sep. 17, 2005.
Gwinner et al., Pivotal role of xanthine oxidase in the initiation of tubulointerstitial renal injury in rats with hyperlipidemia, Kidney International, vol. 69, No. 3, pp. 481-487, 2006.
Halevy et al., Allopurinol is the most common cause of Stevens-Johnson syndrome and toxic epidermal necrolysis in Europe and Israel, J Am ACAD Dermatol, pp. 25-32, Jan. 2008.
Hande et al., Severe Allopurinol Toxicity Description of Guidelines for prevention on Patients with Renal Insufficiency, The American Journal of Medicine, vol. 76, pp. 47-76, Jan. 1984.
Hartung, R., Nephrolithiasis in hyperuricemia and gout, Aktuelle Endokrinologie Und Stoffwechsel, (1982) vol. 3, Issue 4, pp. 164-167.
Heilberg, I.P. et al., Renal Stone Disease: Causes, Evaluation and Medical Treatment, Arq Bras Endocrinol Metab, vol. 50, No. 4, pp. 823-831, Aug. 2006.
Hjortnaes et al., Serum Uric Acid is a Strong Predictor for Stroke in Patients with Metabolic Syndrome, 34:9, pp. 1882-1187, 2007.
Holder et al., Cutaneous and Systemic Manifestations of Drug-Induced Vacuities, The Annals of Pharmacotherapy, vol. 36, pp. 130-147, Jan. 2002.
Horiuchi, H. et al., "A comparative study on the hypouricemic activity and potency in renal xanthine calculus formation of two xanthine oxidase/xanthine dehydrogenase inhibitors: TEI-6720 and allopurinol in rats," Res Commun Mol Pathol Pharmacol (1999) 104(3):307-319.
Horiuchi, H. et al., "Allopurinol increases ear swelling and mortality in a dinitrofluorobenzene-induced contact hypersensitivity mouse model." Biol Pharm Bull (1999) 22(8):810-815.
Horiuchi, H. et al., "Allopurinol induces renal toxicity by impairing pyrimidine metabolism in mice." Life Sci (2000) 66(21):2051-2070.
Horiuchi, H. et al., "Hypouricemic activity of a novel xanthine oxidase/xanthine dehydrogenase (XOD/XDH) inhibitor, TE1-6720 in rats" [abstract]. Jpn J Pharmacol. 2000; 82(Suppl 1):271P. Abstract No. P-606.

(56) References Cited

OTHER PUBLICATIONS

Horiuchi, H. et al., "Nephrotoxic effects of allopurinol in dinitrofluorobenzene-sensitized mice: Comparative studies on TEI-6720." Res Commun Mol Pathol Pharmacol 1999; 104(3):293-305.
Hoshide S et al., Metabolites of TMX-67, a new pharmaceutical entity for the treatment of gout or hyperuricemia, and their pharmacokinetic profiles in humans [abstract].Drug Metab Rev. 2000;32(Suppl 2):269. Abstract No. 266.
Hoshide, S. et al., "PK/PD and safety of a single dose of TMX-67 (febuxostat) in subjects with mild and moderate renal impairment." Nucleosides Nucleotides Nucleic Acids. Oct. 2004; 23(8-9):1117-1118.
Hou, M. et al., "Acute effects of febuxostat, a nonpurine selective inhibitor of xanthine oxidase, in pacing induced heart failure." J Cardiovasc Pharmacol (2006) 48(5):255-263.
Hung et al., HBL-B 5801 allele as a genetic marker for severe cutaneous adverse reactions caused by allopurinol, PNAS, vol. 102, No. 11, pp. 4134-4139, Mar. 15, 2005.
Hydroxyakalone, Drug Print Report, http://release2..i.../reports.print_display?i_query_id=121472&templates=DrugPrint&id=2091, Jan. 17, 2003, 2 pages.
Ioachimescu et al., Serum Uric Acid is an Independent Predictor of All-Cause Mortality in Patients at High Risk of Cardiovascular Disease, Arthritis & Rheumatism, vol. 58 No. 2, pp. 623-630, Feb. 2008.
Iseki et al., Significance of Hyperuricemia as a Risk Factor for Developing ESRD in a Screened Cohort, American Journal of Kidney Disease, vol. 44, No. 4, pp. 642-650, Oct. 2004.
Iseki et al.,Significance of Hyperuricemia on the Early Detection of Renal Failure in a Cohort of Screened Subjects, Hypertens Res., vol. 24, No. 6, pp. 691-697, 2001.
Ishibuchi, S. et al., "Synthesis and structure—activity relationships of 1-phenylpyrazoles as xanthine oxidase inhibitors," Bioorg Med Chem Lett (2001) 11(7):879-882.
Ishiwata Y et al., TMX-67 a novel xanthine oxidase/xanthine dehydrogenase inhibitor, shows strong uric acid lowering action in patients with hyperuricemia and gout [abstract]. Arthritis Rheum. Sep. 2001;44(Suppl 9):S129. Abstract No. 459.
Jeske et al., In vitro Profiling of the Effects of Febuxostat on Hemostatic Parameters, Hemostasis Research laboratories, Dec. 28, 2005, 22 pages.
Jordan, N. et al., "Febuxostat: a safe and effective therapy for hyperuricemia and gout", Future Rheumatology, (2006) 1(3):303-309.
Joseph-Ridge, N., Phase II, dose-response, safety and efficacy clinical trial of a new oral xanthine oxidase inhibitor TMX-67 (febuxostat) in subjects with gout [abstract]. Arthritis Rheum. Sep. 2002; 46(9 Suppl):S142. Abstract No. 289.
Jungers, et al., ESRD Caused by Nephrolithaisis—Prevalence, Mechanisms, and Prevention, American Journal of Kidney Diseases, vol. 44, No. 5, pp. 691-805, Nov. 2004.
Kamatani, N. et al., "Febuxostat, a novel non-purine selective inhibitor of xanthine oxidase, in a phase III placebo-controlled double-blind clinical trial in Japanese subjects with gout or hyperuricemia" [abstract]. Arthritis Rheum. Sep. 2004; 50(9 Suppl):S337. Abstract No. 805.
Kamatani, N. et al., "Febuxostat, a novel non-purine selective inhibitor of xanthine oxidase, in a phase 111 placebo-controlled double-blind clinical trial with gout or hyperuricemia" [in Japanese] [abstract]. Gout and Nucleic Acid Metabolism. 2005; 29(1):68.
Kamatani, N. et al., "Febuxostat, a novel non-purine selective inhibitor of xanthine oxidase, in an allopurinol-controlled phase III clinical trial in Japanese subjects with gout or hyperuricemia" [abstract]. Arthritis Rheum. Sep. 2004; 59(9 Suppl):S336-S337. Abstract No. 804.
Kamatani, N. et al., "Phase II clinical trial using febuxostat (TMX-67), a novel-type xanthine oxidase/xanthine dehydrogenase inhibitor, for gout and hyperuricemia" [in Japanese] [abstract]. Gout and Nucleic Acid Metabolism. 2004; 28(1):38.
Kamatani, N. et al., "Phase II dose-response clinical trial using febuxostat (TMX-67), a novel-type xanthine oxidase/xanthine dehydrogenase inhibitor, for gout and hyperuricemia" [abstract]. Arthritis Rheum. Sep. 2003; 48(9 Suppl):S530. Abstract No. 1349.
Kang et al., Uric Acid and Chronic Renal Disease: Possible Implication of Hyperuricemia on Progression of Renal Disease, D. Kang T. Nakagawa, pp. 43-49, 2005.
Kelley et al., Effect of Allopurinol and Oxipurinol on Pyrimidine Synthesis in Cultured Human Fibroblasts, Biochemical Pharmacology, vol. 20, pp. 1471-1478, 1971.
Khosravan, R. et al., "Dose-related decreases in uric acid observed in a multiple-dose safety, pharmacokinetic, and pharmacodynamic study of TMX-67, a novel xanthine oxidase/dehydrogenase inhibitor, in healthy subjects" [abstract]. Arthritis Rheum. Sep. 2000; 43(9 Suppl):S401. Abstract No. 2009.
Khosravan, R. et al., Effect of concomitant administration of febuxostat and colchicine on pharmacokinetics of febuxostat and colchicine at steady state [abstract]. Arthritis Rheum. Sep. 2005; 52(9 Suppl):S102-S103. Abstract No. 188.
Khosravan, R. et al., "Effect of concomitant administration of febuxostat with naproxen or indomethacin on pharmacokinetics of febuxostat, naproxen, or indomethacin at steady state" [abstract]. Arthritis Rheum. Sep. 2005; 52(9 Suppl):S103. Abstract No. 189.
Khosravan R et al., Effect of febuxostat on pharmacokinetics and pharmacodynamics of warfarin [abstract].J Clin Pharmacol. Sep. 2005;45(9):1084. Abstract No. 71.
Khosravan, R. et al., "Effect of febuxostat on pharmacokinetics of desipramine, a CYP2D6 substrate, in healthy subjects" [abstract]. Clin Pharmacol Ther. Feb. 2005; 77(2):P43. Abstract No. PI-137.
Khosravan, R. et al., "Effect of food or antacid on febuxostat pharmacokinetics and pharmacodynamics in healthy subjects" [abstract]. Clin Pharmacol Ther. Feb. 2005; 77(2):P50. Abstract No. PI-161.
Khosravan, R. et al., "Effect of food or antacid on febuxostat pharmacokinetics and pharmacodynamics in healthy subjects" [abstract]. Pharmacotherapy Mar. 2006; 26:e24. Abstract No. 96E.
Khosravan, R. et al., "Effect of food or antacid on pharmacokinetics and pharmacodynamics of febuxostat in healthy subjects." Br J Clin Pharmacol (2007) 65(3):355-363.
Khosravan, R. et al., "Effect of mild and moderate hepatic impairment on pharmacokinetics, pharmacodynamics, and safety of febuxostat" [abstract]. J Clin Pharmacol. Sep. 2005; 45(9):1083. Abstract No. 69.
Khosravan, R. et al., "Effects of age and gender on febuxostat pharmacokinetics, pharmacodynamics, and safety in healthy subjects" [abstract]. Clin Pharmacol Ther. Feb. 2005; 77(2):P50. Abstract No. PI-162.
Khosravan, R. et al., "Febuxostat, a non-purine selective inhibitor of xanthine oxidase—effect of mild and moderate hepatic impairment on pharmacokinetics, pharmacodynamics, and safety" [abstract]. Arthritis Rheum. Sep. 2004; 50(9 Suppl):S337. Abstract No. 806.
Khosravan, R. et al., "Febuxostat, a novel non-purine selective inhibitor of xanthine oxidase—effect of renal impairment on pharmacokinetics, pharmacodynamics, and safety" [abstract]. J Clin Pharmacol. Oct. 2004; 44(10):1195. Abstract No. 45.
Khosravan, R. et al., "Pharmacokinetic interactions of concomitant administration of febuxostat and NSAIDs." J Clin Pharmacol. Aug. 2006; 46(8):855-866.
Khosravan, R. et al., "Pharmacokinetics, pharmacodynamics and safety of febuxostat, a non-purine selective inhibitor of xanthine oxidase, in a dose escalation study in healthy subjects." Clin Pharmacokinet. 2006;45(8):821-841.
Khosravan, R. et al., "Population pharmacokinetics and pharmacodynamics of febuxostat in a phase-II study of patients with gout" [abstract]. J Clin Pharmacol. Sep. 2005; 45(9):1083. Abstract No. 70.
Khosravan, R. et al., "Population pharmacokinetics and pharmacodynamics of febuxostat in a phase-III study of patients with gout" [abstract]. Clin Pharmacol Ther. Feb. 2006; 79(2):P21. Abstract No. PI-55.
Khosravan, R. et al., "The effect of age and gender on pharmacokinetics, pharmacodynamics, and safety of febuxostat, a novel nonpurine selective inhibitor of xanthine oxidase." J Clin Pharmacol. Sep. 2008; 48(9);1014-1024.

(56) References Cited

OTHER PUBLICATIONS

Khosravan, R. et al., "The effect of mild and moderate hepatic impairment on pharmacokinetics, pharmacodynamics, and safety of febuxostat, a novel nonpurine selective inhibitor of xanthine oxidase." J Clin Pharmacol. Jan. 2006; 46(1):88-102.

Komoriya, K. et al., Hypouricemic effect of allopurinol and the novel xanthine oxidase inhibitor TEI-6720 in chimpanzees. Eur J Pharmacol (1993) 250(3):455-460.

Komoriya, K. et al., "Pharmacokinetics and pharmacodynamics of febuxostat (TMX-67), a non-purine selective inhibitor of xanthine oxidase/xanthine dehydrogenase (NPSIXO) in patients with gout and/or hyperuricemia." Nucleosides Nucleotides Nucleic Acids (2004) 23(8-9):1119-1122.

Komoriya, K. et al., Hypouricemic effect of a novel XOD inhibitor TEI-6720 in chimpanzees [in Japanese] [abstract]. Ryumachi. 1993;33:704.

Kondo, S. et al., "Hypouricemic effects of TMX-67 (TEI-6720), a novel xanthine dehydrogenase/oxidase inhibitor, in rats and chimpanzees" [abstract]. Clin Biochem. Apr. 1997; 30(3):264. Abstract No. 90.

Krenitsky et al., Inhibition of Human Purine Nucleoside Phosphorylase, The Journal of Biological Chemistry, vol. 243, No. 11, pp. 2870-2881, 1968.

Krishnan et al., Long-term Cardiovascular Mortality Among Middle-aged Men with Gout, Arch Intern Med., vol. 168, No. 10, pp. 1104-1110, May 26, 2008.

Krishnan, Gout and Coronary Artery Disease—Epidemiologic Clues, Current Rheumatology Reports, vol. 10, pp. 249-255, 2008.

Kubo, J. et al., "Pharmacodynamics of TMX-67 (TEI-6720), a novel xanthine [sic] dehydrogenase/oxidase inhibitor, in man" [abstract]. Clin Biochem. (1997) 30(3):265. Abstract No. 93.

Kukulka, M. et al., "Effects of age and gender on febuxostat pharmacokinetics, pharmacodynamics, and safety in healthy subjects" [abstract]. Pharmacotherapy. Apr. 2006; 26(4):e23-e24. Abstract No. 95E.

Lawrence et al., Estimates of the Prevalence of Arthritis and Other Rheumatic Conditions in the United States, Arthritis & Rheumatism, Vo. 58, No. 1, pp. 26-35, Jan. 2008.

Lee et al., Allopurinol Hypersensitivity syndrome: A Preventable Severe Cutaneous Adverse Reaction, Singapore Med J., 49(5), pp. 384-387, 2008.

Lee et al., Serum uric Acid is Associated with Microalbuminura in Prehypertension, Hypertension, vol. 47, pp. 962-967, 2006.

Lehto et al., Serum Uric Acid is a Strong Predictor of Stroke in Patients with Non-Insulin-Dependent Diabetes Mellitus, American Heart Association, pp. 635-639, 1998.

Lieske, J.C. et al., "Renal stone epidemiology in Rochester, Minnesota: An update," Kidney International (2006) 69:760-764.

Liu-Bryan et al., "Evil humors take their toll as innate immunity makes gouty joints TREM-ble," Arthritis & Rheum. Feb. 2006; 54(2):383-386.

Li-Yu et al., Treatment of Chronic Gout. Can we Determine when Urate Stores are Depleted Enough to Prevent Attacks of Gout?, The Journal of Rheumatology, 28:3, pp. 557-580, 2001.

Lonjou et al., A European study of HLA-B in Stevens-Johnson syndrome and toxic epidermal necrolysis related to five high-risk drugs, Pharmacogenetics and Genomics, vol. 18, No. 2, pp. 99-107, 2008.

MacDonald, P.A. et al., "Febuxostat versus allopurinol versus placebo in the treatment of gout in African-American subjects" [abstract]. J Natl Med Assoc. Aug. 2006; 98(8):1389-1390.

MacDonald, P.A. et al., "Febuxostat vs. allopurinol and placebo in subjects with hyperuricemia and gout: the 28-week APEX study" [abstract]. Pharmacotherapy Oct. 2006; 26(10):e94. Abstract No. 267E.

Manfredi, R.L. et al., "Inhibition of theophylline metabolism by long-term allopurinol administration," Clin. Pharmacol. Ther. (1981) 29(2):224-229.

Mayer, M.D. et al., "Pharmacokinetics and pharmacodynamics of febuxostat, a new non-purine selective inhibitor of xanthine oxidase in subjects with renal impairment." Am J Ther. Jan.-Feb. 2005; 12(1):22-34.

Mazzali, M. et al., "Elevated uric acid increases blood pressure in the rat by a novel crystal-independent mechanism." Hypertension (2001) 38:1101-1106.

Mazzali et al., Hyperuricemia induces a primary arteriolopathy in rats by a blood pressure-independent mechanism, Am J Physiol Renal Physiol, 282, pp. F991-F997, 2002.

McDonald, P.A., et al., "Febuxostat versus allopurinol controlled trial in subjects with hyperuricemia and gout (FACT): a multicenter, phase 3, randomized, controlled, double-blind clinical study" [abstract]. Consult Pharm. Jan. 2006; 21(1):77.

McKendrick et al., Allopurinol hypersensitivity, British Medical Journal, p. 998, Apr. 14, 1979.

Melethil, S. et al., "Steady state urinary excetion of theophylline and its metabolites in the presence of erythromycin." Res. Commun Chem. Pathol. Pharmacol. (1982) 35(2):341-344.

Merck Manual, The, 17th edition (Japanese version), Nikkei Business Publications, Inc. (1999) 464-468.

Miyamoto, Y. et al., "Potentiation of Nitric Oxide-Mediated Vasorelaxation by Xanthine Oxidase Inhibitors (43982)", NO-Mediated Vasorelaxation, Proceedings of the Society for Experimental Biology and Medicine (1996) 211(4):366-373.

Mockenhaupt et al., Stevens-Johnson Syndrome and Toxic Epidermal Necrolysis: Assessment of Medication Risks with Emphasis on Recently Marked Drugs. The EuroSCAR-Study, Journal of Investigative Dermatology, vol. 128, pp. 35-44, 2008.

Moriwaki, Y., et al. Study on crystal polymorphism of TEI-6720 [in Japanese] [abstract]. Journal of Pharmaceutical Science and Technology, Japan. 2002;62(Suppl):279.

Mukoyoshi, M. et al., "In vitro drug-drug interaction studies with febuxostat, a novel non-purine selective inhibitor of xanthine oxidase: plasma protein binding, identification of metabolic enzymes and cytochrome P450 inhibition," Xenobiotica (2008) 38(5):496-510.

Nakagawa et al., Uric Acid—A Uremic Toxin, Blood Purif, 24, pp. 67-70, 2006.

Nakagawa, T. et al., "A casual role for uric acid in fructose-induced metabolic syndrome," Am. J. Physiol. Renal Physiol. (2006) 290:F625-631.

National Kidney Foundation, "Definition and Classification of Stages of Chronic Kidney Disease," American Journal of Kidney Diseases, vol. 39, No. 2, Suppl 1, pp. S46-S75, Feb. 2002.

National Kidney Foundation, "What you need to know about urinalysis," (2002) 1-10.

Newaz, M.A. et al., "Uric acid, xanthane oxidase and other risk factors of hypertension in noormotensive subjectives," CAS accession #1996:571720, Clinical and experimental hypertension (1996) 18:1035-1050.

Ochiai et al., Uric Acid Renal Excretion and Renal Insufficiency in Decompensated Severe Heart Failure, The European Journal of Heart Failure 7, pp. 468-474, 2005.

Okamoto et al., An Extremely Potent Inhibitor of Xanthine Oxidoreductase, Crystal Structure of the Enzyme-Inhibitor Complex and Mechanism of Inhibition, The Journal of Biological Chemistry, vol. 278, No. 3, pp. 1848-1855 (2003).

Osada, Y. et al., "Hypouricemic effect of the novel xanthine oxidase inhibitor, TEI-6720, in rodents." Eur J Pharmacol (1993) 241(2/3):183-188.

Ouyang et al., Fructose Consumption as a risk factor for Non-Alcoholic fatty liver disease, Journal of Hepatology, vol. 48, pp. 993-999, 2008.

Pacher et al., Pharm Rev. (2006) 58:87-114.

Padang et al., Characteristics of Chronic Gout in Northern Sulawesi, Indonesia, The Journal of Rheumatology, 33:9, pp. 1813-1817, 2006.

Patetsios et al., Identification of Uric Acid and Xanthine Oxidase in Atherosclerotic Plaque, The American Journal of Cardiology, vol. 88, pp. 188-191, Jul. 15, 2001.

Peres-Ruiz et al., Using Serum Urate Levels to Determine the Period Free of Gouty Symptoms after withdrawal of long-term Urate-Low-

(56) References Cited

OTHER PUBLICATIONS ering Therapy: A Prospective Study, Arthritis & Rheumatism, vol. 55, No. 5, pp. 786-790, Oct. 15, 2006.
Perez-Ruiz et al., Renal Underexcretion of Uric Acid Is Present in Patients with Apparent High Urinary Uric Acid Output, Arthritis & Rheumatism, vol. 47, No. 6, pp. 610-613, Dec. 15, 2002.
Perez-Ruiz, F. et al., "Effect of urate-lowering therapy on the velocity of size reduction of tophi in chronic gout," Arthr. Rheum. (2002) 47(4):356-360.
Perlstein et al., Uric Acid and the State of Intrarenal renin-angiotensin system in humans, Kidney International, vol. 66, pp. 1465-1470, 2004.
Petersel et al. Treatment of Acute Gout in Hospitalized Patients, The Journal of Rheumatology, 34:7, pp. 1556-1568, 2007.
Pharmaprojects: PHAR PHLP PHDI (PHZZ), BOF-4272, PJB Publications, Ltd, Richmond, UK, (1998) 2 pages.
Pittman, J.R. et al., "Diagnosis and Management of Gout," American Family Physician (1999) 59(7):1799-1806.
R&D Insight, BOF 4272, Adis International, 2003, 3 pages.
R&D Insight, Research programme, Adis International Ltd., 2003, 2 pages.
Reinders et al., Biochemical effectiveness of allopurinol and allopurinol-probenecid in Previously Benzbromarone-treated gout Patients, Clin Rheumatol, 26, pp. 1459-1465,2007.
Reyes, The Increase in Serum Uric Acid Concentration caused by diuretics might be beneficial in heart failure, The European Journal of Heart Failure, vol. 7, pp. 461-467, 2005.
Robert, Predictability of creatinine Clearance estimates in critically ill patients, Critical Care Medicine, vol. 21, No. 10, pp. 1487-1495, 1993.
Sanchez-Lozada, L.G. et al., "Effects of febuxostat on metabolic and renal alterations in rats with fructose-induced metabolic syndrome." Am J Physiol Renal Physiol. 2008 294:F710-F718.
Sanchez-Lozada, L.G. et al., Treatment with the xanthine oxidase inhibitor febuxostat lowers uric acid and alleviates systemic and glomerular hypertension in experimental hyperuricaemia. Nephrol Dial Transplant. (2008) 23:1179-1185.
Sanchez-Lozada, L.G. et al., "Effect of febuxostat on the progression of renal disease in 5/6 nephrectomy rats with and without hyperuricemia." Nephron Physiol (2008) 108:p. 69-p. 78.
Sanchez-Lozada, L.G. et al., "Effect of febuxostat on the progression of renal disease in 5/6 Nx rats with and without hyperuricemia" [abstract]. J Am Soc Nephrol. Oct. 2007; 18:400A. Abstract No. SA-PO262.
Sarawate et al., "Serum Urate Levels and Gout Flares Analysis From Managed Care Data," Journal of Clinical Rheumatology, vol. 12, No. 2, pp. 61-65, Apr. 2006.
Sarawate et al., Gout medication Treatment Patterns and Adherence to Standards of Care from a managed Care Perspective, Mayo Clin Proc. vol. 81(7), pp. 925-934, Jul. 2006.
Sato, S. et al. "A Novel Xanthine Dehydrogenase Inhibitor (BOF-4272)," Purine and Pyrimidine Metabolism in Man, ed. By R.A. Harkness, Plenum Press, NY (1991) VII, Part A, 135-138.
Schlesinger et al., Gout Can management be improved?, Current Opinion in Rheumatology, vol. 13, pp. 240-244, 2001.
Schlesinger et al., Update on Gout, Arthritis & Rheumatism, vol. 47, No. 5, pp. 563-565, Oct. 15, 2002.
Schneider, H.J. et al., "Prevention of recurrent uric acid and calcium oxalate stones by administration of the xanthine oxidase inhibitors Milurit 100 and Milurit 300," International Urology and Nephrology, (1983) 15(2):121-129.
Schumacher, H.R. et al., "A phase 2, long term open-label safety and efficacy study of febuxostat, a novel non-purine, selective inhibitor of xanthine oxidase" [abstract]. Arthritis Rheum. Sep. 2004; 50(9 Suppl):S335. Abstract No. 800.
Schumacher, H.R. et al., "Direct physical measurement method for evaluation of tophus nodules in subjects with gout" [abstract]. Arthritis Rheum. Sep. 2003; 48(9 Suppl):S637-S638. Abstract No. 1664.
Schumacher, H.R. et al., "Febuxostat vs. allopurinol and placebo in subjects with hyperuricemia and gout: the 28-week APEX study" [abstract]. Arthritis Rheum. Sep. 2005; 52(9 Suppl):S680. Abstract No. 1837.
Schumacher, H.R. et al., "Long-term safety and efficacy of febuxostat, a novel non-purine selective inhibitor of xanthine oxidase, in subjects with hyperuricemia and gout" [abstract]. Ann Rheum Dis. Jul. 2005; 64(Suppl 3):498. Abstract No. SAT0282.
Schumacher, H.R. et al., "Magnetic resonance imaging of gouty tophi during treatment with febuxostat, a non-purine selective inhibitor of xanthine oxidase" [abstract]. Arthritis Rheum. Sep. 2004; 50(9 Suppl):S336. Abstract No. 802.
Schumacher, H.R. Jr, et al., Effects of febuxostat versus allopurinol and placebo in reducing serum urate in subjects with hyperuricemia and gout: A 28-week, phase III, randomized, double-blind, parallel-group trial. Arthritis Care Res. Nov. 2008; 59(11):1540-1548.
Schumacher, H.R. Jr, et al., "Febuxostat (FEB) versus Allopurinol (ALLO) in the Treatment of Gout in Subjects >= 65 Years of Age" [abstract]. J Am Geriatr Soc. Apr. 2008; 56(s1):S126. Abstract No. C44.
Schumacher, H.R. Jr, et al., "Febuxostat in the treatment of gout: 5-yr findings of the FOCUS efficacy and safety study." Rheumatology (2009) 48(2):188-194.
Schumacher, H.R. Jr, et al., "Febuxostat versus allopurinol in the treatment of gout in subjects 65 years of age or older" [abstract]. Ann Rheum Dis. Jul. 2007; 66(Suppl II):234-235. Abstract No. THU0353.
Schumacher, H.R. Jr, et al., "Long-term efficacy and safety of febuxostat (FEB) in patients with gout: results of the five-year Focus study" [abstract]. J Clin Rheumatol. Aug. 2008; 14(4):S4.
Schumacher, H.R. Jr, et al., "Magnetic resonance imaging in the quantitative assessment of gouty tophi" [erratum in: Int J Clin Pract May 2006; 60(5):630]. Int J Clin Pract. Apr. 2006; 60(4):408-414.
Schumacher, H.R. Jr, et al., "Phase 2, long-term, open-label safety and efficacy study of febuxostat, a novel nonpurine, selective inhibitor of xanthine oxidase" [abstract]. J Natl Med Assoc. Jun. 2005; 97(6):901.
Schumacher, H.R. Jr, et al., "Reduction in gout flares and tophus size in the 52-week Febuxostat Allopurinol controlled trial (FACT)" [abstract]. J Clin Rheumatol. Aug. 2006; 12(4 Suppl):S9. Abstract No. 28.
Schumacher, H.R., et al., "The focus trial 48-month interim analysis: long-term clinical outcomes of treatment with febuxostat in subjects with gout in an ongoing phase 2, open-label extension study" [abstract]. Ann Rheum Dis. Jul. 2006; 65(Suppl 2):93. Abstract No. OP0130.
Schumacher, H.R. Jr, et al., "The FOCUS trial 48-month interim analysis: long-term clinical outcomes of treatment with febuxostat in subjects with gout in an ongoing phase 2, open-label extension study" [abstract]. Arthritis Rheum. Sep. 2006; 54(9 Suppl):S319-S320. Abstract No. 703.
Schumacher, H.R. Jr, et al., "Tophaceous gout: quantitative evaluation by direct physical measurement." J Rheumatol. Dec. 2005; 32(12):2368-2372.
Shoji et al., A Retrospective Study of the Relationship Between Serum Urate Level and Recurrent Attacks of Gouty Arthritis: Evidence for Reduction of Recurrent Gouty Arthritis with Antihyperuricemic Therapy, Arthritis & Rheumatism, vol. 51, No. 3, pp. 321-325, Jun. 15, 2004.
Siu, Y. et al., "Use of allopurinol in slowing the progression of renal disease through its ability to lower serum uric acid level." American Journal of Kidney Diseases (2006) 47(1):51-59.
Sorbera, L.A. et al., "TMX-67: Treatment of gout and hyperuricemia, xanthine oxidase inhibitor: TEI-6720," Drugs of the Future (2001) 26(1):32-38.
Sturm et al., Uric Acid as a risk factor for progression of non-diabetic chronic kidney disease? The mild to Moderate Kidney Disease (MMKD) Study, Experimental Gerontology, vol. 43, pp. 347-352, 2008.
Suliman et al., J-Shaped Mortality Relationship for Uric Acid in CKD, American Journal of Kidney Diseases, vol. 48, No. 5, pp. 761-771, Nov. 2006.

(56) References Cited

OTHER PUBLICATIONS

Suzuki, H. et al., "Xanthine oxidase activity associated with arterial blood pressure in spontaneously hypertensive rats." Proc Natl. Acad. Sci. USA, Apr. 1998; 95(8):4754-4759.

Swan, S., et al., "Effect of renal impairment on pharmacokinetics, pharmacodynamics, and safety of febuxostat (TMX-67), a novel non-purine selective inhibitor of xanthine oxidase" [abstract]. Arthritis Rheum. Sep. 2003; 48(9 Suppl):S529. Abstract No. 1348.

Takano, Y. et al. "Selectivity of febuxostat, a novel non-purine inhibitor of xanthine oxidase/xanthine dehydrogenase," Life Sciences (2005) 76(16):1835-1847.

Talaat et al., The Effect of Mild Hyperuricemia on Urinary Transforming Growth Factor Beta and the Progression of Chronic Kidney Disease, American Journal of Nephrology, vol. 27, pp. 435-440, 2007.

Tausche, A-K et al., "The Janus Faces of Allopurinol- Allopurinol Hypersensitivity Syndrome," The American Journal of Medicine, vol. 121, No. 3, pp. e3-e4, Mar. 2008.

Terkeltaub et al., Recent developments in our understanding of the renal basis of hyperuricemia and the Development of Novel Antihyperuricemic Therapeutics, Arthritis Research & Therapy, vol. 8 (Suppl 1), pp. 1-9, 2006.

Terkeltaub, "Gout in 2006. The perfect storm," Bulletin of the NYU Hospital for Joint Diseases, vol. 64, No. 1 & 2, pp. 82-86, 2006.

Terkeltaub, "Gout," The New England Journal of Medicine, 349:17, pp. 1647-1655, Oct. 23, 2003.

Terkeltaub, "Pathogenesis and treatment of crystal-induced inflammation," in Arthritis and Allied Conditions, A Textbook of Rheumatology, vol. 2, pp. 2329-2347, 2001.

Thomson Current Drugs, Patent Report for WO-03064410 (2003) 1 page.

Uematsu, T. et al., "Pharmacokinetic and Pharmacodynamic Properties of a Novel Xanthine Oxidase Inhibitor, BOF-4272, in Healthy Volunteers," J. Pharm. Exp. Ther. (1994) 270(2):453-459.

Wallace et al., Preliminary Criteria for the Classification of the Acute Arthritis of Primary Gout, Arthritis and Rheumatology, vol. 20, No. 3, pp. 895-900, Apr. 1977.

Wallace et al., Therapy in Gout, Rheumatic Disease Clinics of North America, vol. n14, No. 2, pp. 441-457, Aug. 1988.

Website pages from www.marvistavent.com, regarding CARPROFEN, Brand Name: RIMADYL, Jul. 24, 2006.

Whelton, A. et al., "Beneficial relationship of serum urate (sUA) reduction and estimated glomerular filtration Rate (eGFR) improvement/maintenance in hyperuricemic gout subjects treated for up to 5.5 years with febuxostat (FEB)" [abstract]. Arthritis Rheum. Dec. 2008; 58(12):3975. Abstract No. L7.

Whelton, A. et al., "Febuxostat, a novel non-purine selective inhibitor of xanthine oxidase, in patients with a history of nephrolithiasis" [abstract]. J Am Soc Nephrol. (2006) 17:525A. Abstract No. F-PO894.

Whelton, A. et al., "Patients with gout and a history of nephrolithiasis, treated with febuxostat, a novel non-purine selective inhibitor of xanthine oxidase, for more than 5 Years" [abstract]. Ann Rheum Dis. Jul. 2007; 66(Suppl II):624. Abstract No. AB0749.

Worcester, E.M. et al., "Renal function in patients with nephrolithiasis," J. Urology (2006) 176(2):600-603.

Wortmann, R. et al., "Gout flare prophylaxis during management of chronic gout with febuxostat, a non-purine selective inhibitor of xanthine oxidase" [abstract]. Arthritis Rheum. Sep. 2004; 50(9 Suppl):S335-S336. Abstract No. 801.

Wortmann, RL et al., "Effect of febuxostat or allopurinol on the clinical manifestations of gout: reduction in gout flares and tophus size over time in the EXCEL trial" [abstract]. Arthritis Rheum. Sep. 2006; 54(9 Suppl):S642. Abstract No. 1592.

Wortmann, R.L. et al., "Gout flare prophylaxis during management of chronic gout with febuxostat, a nonpurine selective inhibitor of xanthine oxidase" [abstract]. J Natl Med Assoc. Jun. 2005; 97(6):895-896.

Wortmann, R.L. et al., "Reduction in tophus size in subjects with chronic gout treated with febuxostat or allopurinol for 52 weeks—FACT trial" [abstract]. Arthritis Rheum. Sep. 2005; 52(9 Suppl):S108. Abstract No. 203.

Wortmann, R.L. "Recent advances in the management of gout and hyperuricemia," Current Opinion in Rheumatology (2005) 17(3):319-324.

Xanthine oxidase inhibitors, Yamasa Shyoyu, Drug Print Report, http://release2.i.../reports.print_display?i_query_id=1214721 &template=DrugPrint&id=1093, Jan. 17, 2003, 2 pages.

Xu, X. et al., "Xanthine Oxidase Inhibition with Febuxostat Attenuates Systolic Overload-Induced Left Ventricular Hypertrophy and Dysfunction in Mice." J Cardiac Fail (2008) 14(9):746-753.

Xu, X. et al., "Delayed Treatment Effects of Xanthine Oxidase Inhibition on Systolic Overload-Induced Left Ventricular Hypertrophy and Dysfunction," Takeda Global Research & Development Center, Inc., Deerfield, IL. Presented at the 13th International Symposium on Purine and Pyrimidine Metabolism in Man, Stockholm, Sweden, Jun. 21-24, 2009. Nucleosides Nucleotides and Nucleic Acids (2010) 29:306-313.

Yamaguchi, S., "Treatment for hyperuricosemia in patients with urolithiasis including uric acid stone," Progress in Medicine (2004) 24(5):1213-1218 (Japanese Publication).

Yamamoto, T. et al., Effect of TEI-6720, a xanthine oxidase inhibitor, on the nucleoside transport in the lung cancer cell line A549. Pharmacology 2000 60:34-40.

Yasui, T. et al., "Effects of Allopurinol on Renal Stone Formation and Osteopontin Expression in a Rat Urolithiasis Model" [abstract]. Nephron (2001) 87(2):170-176.

Yonezawa, H. et al., "Pharmacokinetics of TMX-67 (TEI-6720), a novel xanthine dehydrogenase/oxidase inhibitor, in man" [abstract]. Clin Biochem. Apr. 1997; 30(3):296-297. Abstract No. 221.

Yu, P. et al., "Effect of febuxostat, a novel non-purine, selective inhibitor of xanthine oxidase, on the QT interval in healthy subjects" [abstract]. J Clin Pharmacol. Oct. 2004; 44(10):1195. Abstract No. 46.

Zhang, W., "EULAR evidence based recommendations for gout. Part 1: Diagnosis. Report of a Task Force of the Standing Committee for International Clinical Studies including Therapeutics (ESCISIT),", Ann Rheum Dis 2006; 65, pp. 1301-1311.

Zhao, L. et al., "Chronic xanthine oxidase inhibition following myocardial infarction in rabbits: effects of early versus delayed treatment." Life Sci. (2008) 82:495-502.

Zhao L et al., Effect of febuxostat, a novel non-purine, selective inhibitor of xanthine oxidase (NP-SIXO), on enzymes in purine and pyrimidine metabolism [abstract]. Arthritis Rheum. Sep. 2003;48(9 Suppl): S531. Abstract No. 1352.

Zhao, L. et al., "Febuxostat, a non-purine selective inhibitor of xanthine oxidase, has a voltage-dependent agonist effect on hERG potassium currents" [abstract]. Heart Rhythm. May 2006; 3(5 Suppl):S261. Abstract No. P5-4.

Zoellner et al., "Allopurinol in the Treatment of Gout and Uric Acid Nephrolithiasis" abstract, Deutsche Medizinische Wochenschrift, 1967, vol. 92, No. 14, pp. 654-660.

Zoellner, "Treatment of Gout and Urate Nephrolithiasis with Allopurinol" Verhandlungen der Deutschen Gesellschaft fuer Innere Medizin, vol. 72, pp. 781-786 (1967).

United States Patent Office Action for U.S. Appl. No. 11/939,112 dated Oct. 27, 2011 (18 pages).

United States Patent Office Action for U.S. Appl. No. 11/939,112 dated Feb. 1, 2011 (12 pages).

United States Patent Office Action for U.S. Appl. No. 12/015,527 dated Aug. 17, 2011 (14 pages).

United States Patent Office Action for U.S. Appl. No. 12/015,527 dated Nov. 9, 2010 (10 pages).

United States Patent Office Action for U.S. Appl. No. 11/497,608 dated Mar. 27, 2012 (26 pages).

United States Patent Office Action for U.S. Appl. No. 11/497,608 dated Apr. 29, 2009 (10 pages).

United States Patent Office Action for U.S. Appl. No. 11/497,608 dated Sep. 12, 2008 (16 pages).

United States Patent Office Action for U.S. Appl. No. 11/497,608 dated Nov. 15, 2007 (9 pages).

(56) References Cited

OTHER PUBLICATIONS

United States Patent Office Action for U.S. Appl. No. 12/689,266 dated Mar. 15, 2012 (20 pages).
United States Patent Office Action for U.S. Appl. No. 11/429,734 dated Oct. 9, 2009 (9 pages).
United States Patent Office Action for U.S. Appl. No. 11/429,734 dated Feb. 12, 2009 (10 pages).
United States Patent Office Action for U.S. Appl. No. 11/429,734 dated Mar. 28, 2008 (13 pages).
United States Patent Office Action for U.S. Appl. No. 12/210,207 dated Sep. 27, 2011 (19 pages).
United States Patent Office Action for U.S. Appl. No. 12/210,207 dated Feb. 7, 2011 (12 pages).
United States Patent Office Action for U.S. Appl. No. 13/295,696 dated Apr. 12, 2012 (10 pages).
International Search Report and Written Opinion for Application No. PCT/US2011/050870 dated Nov. 29, 2011 (14 pages).
International Search Report and Written Opinion from PCT/US08/51248 mailed Jun. 25, 2008 (12 pages).
International Search Report and Written Opinion from PCT/US06/30023 mailed Dec. 7, 2007 (11 pages).
International Search Report and Written Opinion from PCT/US07/84573 mailed Apr. 25, 2008 (8 pages).
International Search Report and Written Opinion from PCT/US06/17663 mailed Nov. 27, 2006 (4 pages).
International Search Report from PCT/US2007/084573 dated Feb. 25, 2008 (6 pages).
European Search Report and Opinion from Application No. 07864338.4 mailed Dec. 29, 2009 (7 pages).
European Search Report and Opinion from Application No. 06759284 mailed Dec. 29, 2009 (12 pages).
Supplementary European Search Report and Opinion from Application No. 06774718.8 mailed Dec. 22, 2009 (11 pages).
Supplementary European Search Report and Opinion from Application No. 07864338.4 mailed Nov. 4, 2009 (13 pages).
Supplementary European Search Report and Opinion from Application No. 08705967 dated Dec. 22, 2009 (7 pages).
Supplementary European Search Report and Opinion reissued from Application No. 06759284 mailed Feb. 16, 2010 (6 pages).
European Patent Office Action for Application No. 07864338.4 dated Jan. 14, 2011 (7 pages).
"Uloric (febuxostat) tablet for oral use" label, Feb. 13, 2009, 17 pages.
U.S. FDA approval letter of uloric to Takeda Pharmaceuticals North America, Inc., NDA 21-856, dated Feb. 13, 2009, 6 pages.
Aucamp, J. et al., "Inhibition of xanthine oxidase by catechins from tea (Camellia sinensis)," Anticancer Res. (1997) 17(6D):4381-4385.
Erokhin, A.P. etal., "Cryptorchidism," Moscow (1995) p. 209, Chapter 5, English translation.
Itoh, Y. et al., "Preventive effects of green tea on renal stone formation and the role of oxidative stress in nephrolithiasis," J. Urology (2005) 173(1):271-275.
Laakso, J.T. et al., "Renal xanthine oxidoreductase activity during development of hypertension in spontaneously hypertensive rats," J. Hypertension (2004) 22(7):1333-1340.
Puig, J.G. et al., "Inhibition of xanthine oxidase by allopurinol: a therapeutic option for ischaemia induced pathological processes," Annals of Rheumatic Diseases (1989) 883-888.
Sonoda, T. et al., "A study on allopurinol in he prevention of recurrent calcium oxalate stones," Hinyoklka Kiyo (1985) 31:2071-2079, English abstract provided.
Svetkey, L.P., "Management of prehypertension," Hypertension (2005) 45:1056-1061.
Takao, S., "Hypertension—its pathological condition and treatment (1) hypertension treatment and guidelines," Medicine and Pharmacy (2003) 50(5):588-594.
Tareeva, I.E., Nephrology. Guide for Physicians. 2nd Edition, Moscow: Meditsina (2000) 422-428.
Traynor, K., "New gout treatment approved," Amer. J. Health-Syst. Pharm. (2009) 66:606-607.

United States Patent Office Action for U.S. Appl. No. 12/015,527 dated Nov. 1, 2013.
United States Patent Office Notice of Allowance for U.S. Appl. No. 13/295,696 dated Dec. 4, 2012 (8 pages).
United States Patent Office Action for U.S. Appl. No. 13/295,696 dated Nov. 6, 2012 (12 pages).
United States Patent Office Action for U.S. Appl. No. 11/429,734 dated Sep. 18, 2013 (16 pages).
United States Patent Office Action for U.S. Appl. No. 12/689,266 dated Oct. 26, 2012 (11 pages).
International Search Report for Application No. PCT/US2011/025450 dated May 2, 2011 (2 pages).
Written Opinion for Application No. PCT/US2011/025450 dated May 2, 2011 (6 pages).
Brennan, M.R. et al., "Comparing rates of dyspepsia with coxibs vs. NSAIDPPI: a meta-analysis," The Amer. J. of Med. (2006) 119:448.e27-448.e36.
Edwards, N.L., "Febuxostat: a new treatment for hyperuricaemia in gout," Rheumatology (2009) 48:ii15-ii19.
Schumacher, H.R., Jr., "The pathogenesis of gout," Cleveland Clin. J. Med. (2008) 75(5):S2-S4.
Zhang, W. et al., "EULAR evidence based recommendations for gout. Part II: Management. Report of a task force of the EULAR Standing Committee for International Clinical Studies Including Therapeutics (ESCISIT)," Ann. Rheum. Dis. (2006) 65:1312-1324.
United States Patent Office Action for U.S. Appl. No. 13/521,765 mailed Feb. 18, 2014 (13 pages).
Reagan-Shaw et al., "Dose translation from animal to human studies revisited," FASEB Journal (2008) 22:659-661.
Response to European Search Report for Application No. 11796331.4 dated Jun. 6, 2014.
Notice of Allowance for U.S. Appl. No. 11/429,734 dated May 30, 2014 (14 pages).
Bernad, Berta et al., "Clinical Image: Corneal tophus deposition in gout," Arthritis & Rheumatism, vol. 54, Issue 3, Mar. 2006, p. 1025.
Edwards, Lawrence N., "Management of Hyperuricemia," vol. 115, published prior to at least Sep. 8, 2011, pp. 2314-2328.
Hershfield, Michael S., "Gout and Uric Acid Metabolism," Textbook of Medicine, $21^{st}$ Edition, vol. 2, Jan. 2000, pp. 1541-1548.
Mochizuki, H. et al., Polymorphism studies of TEI-6720, Abstract, AAPS Pharm. Sci., vol. 3(S1), 2001, 1 page.
Rosenberg, Andrew E. M.D., "Skeletal System and Soft Tissue Tumors," Pathologic Basis of Disease, $5^{th}$ Edition, Chapter 27, Jun. 1995, pp. 1213-1271.
Wortmann, Robert L., "Gout and Other Disorders of Purine Metabolism," In: Brunwald E, editor, Harrison's Principles of Internal Medicine, $14^{th}$ Edition, Chapter 344, 1998, pp. 2158-2166.
Alstott, R.L. et al., "The acute toxicities of 1-methylxanthine, ethanol and 1-methylxanthine/ethanol combinations in the mouse," Toxicology & Applied Pharmacology (1973) 24:393-404.
Badyal, D.K., "Cytochrome P450 and drug interations," Indian J. of Pharm. (2001) 33:248-259.
Barnes, P.J., "Theophylline," (2010) 3:725-747.
Birkett, D.J. et al., "1-Methylxanthine derived from caffeine as a pharmacodynamic probe of oxypurinol effect," Br. J. Clin. Pharmacol. (1997) 43:197-200.
Burkowskyj, M. et al., "Theophylline reassessed," Annals of Int. Med. (1984) 101(1):63-73.
Byrn, S. et al., "Pharmaceutical Solids: a strategic approach to regulatory considerations," Pharm. Res. (1995) 12(7):945-954.
Byrn, S.R. et al., Solid-State Chemistry of Drugs, "Properties of amorphous solids," (1999) 2nd Edition, p. 22.
Cornish, H.H. et al., "The study of metabolism of theoloromine, theophylline and caffeine in man," Metabolism of Methylated Xanthines (1957) 228:315-323.
Farag Badawy, S. et al., "Effct of drug substance eparticle size on the characteristics of granulation manufactured in a high-shear mixer," AAPS Pharm. Sci. Tech. (2000) 1(4):55-61.
Hasegawa, M., "A facile one-pot synthesis of 4-alkoxy-1,3-benzenedicarbonitrile," Heterocycles (1998) 47:857-864.
Jillavenkatesa, A. et al., "Particle size characterization," Special Publication of National Institute of Standards and Technology (2001) 960-1:83-85.

(56) References Cited

OTHER PUBLICATIONS

Kalra, B.S., "Cytochrome P450 enzyme isoforms and their therapeutic implications: an update," Indian J. Med. Sci. (2007) 61:102-116.
Kibbe, A., Handbook of Pharm. Excipients, American Pharmaceutical Association and Pharmaceutical Press (2000), "Hydroxypropyl cellulose," 244-248, "Lactose," 276-285, "Propylene glycol," 442-444, "Starch, pregelatinized," 528-530.
Kitamura, H., "Effects of solvent composition and temperature on polymorphism and crystallization behavior of thiazole-derivative," J. Crystal Growth (2002) 236:676-686.
Lantz, R.J. et al., "Size reduction," Pharmaceutical Dosage Forms, Tablets, vol. II, p. 107-112, H.A. Lieberman editor, Marcel Dekker, Inc., New York (1990).
Rodopoulos, N. et al., "Elimination of theophylline metabolites in healthy adults," Scand. J. Clin. Lab. Invest. (1997) 57:233-240.
Theolair Package Insert, Mosby's GenRx, 8th edition, Mosby-Yearbook Inc., St. Louis, MO (May 1998) 13 pages.
U.S. Department of Health and Human Services, Center for Drug Evaluation and Research, "Guidance for Industry: estimating the maximum safe starting dose in initial clinical trials for therapeutics in adult healthy volunteers," FDA Guidance (2005) 30 pages.
U.S. Department of Health and Human Services, Center for Drug Evaluation and Research, "Guideline for Submitting Supporting Documentation in Drug Applications for the Manufacture of Drug Substances," (1997) 21 pages.
Van Gennip, A.H., "Urinary excretion of 3-methylxanthine and related compounds in children," Clin Chimica Acta (1973) 45:119-127.
Yamamoto, K. et al., "Neurotoxic convulsions induced by theophylline and its metabolites in mice," Biol. Pharm. Bull. (1996) 19(6):869-872.
Yang, K.H., "Effects of CYP inducers and inhibitors on the pharmacokinetics of intravenous theophylline in rats: involvement of CYP1A1/2 in the formation of 1.3-DMU," J. Pharm. Pharmacology (2008) 60:45-53.
Yonemochi, E. et al., "Physicochemical properties of amorphous clarithromycin obtained by grinding and spray drying," Eur. J. Pharm. Sci. (1999) 7(4):331-338.
Complaint, U.S. District Court, District of Delaware, Case No. 14-CV-00184, *Teijin Limited* et al. vs. *Lupin Ltd.* et al. (Feb. 12, 2014).
Answer, Defenses and Counterclaims of Defendants' Lupin Ltd. and Lupin Pharmaceuticals, Inc., U.S. District Court, District of Delaware, Case No. 14-CV-00184, *Teijin Limited* et al. vs. *Lupin Ltd.* et al. (Apr. 1, 2014).
Plaintiff/Counterclaim Defendants Teijins and Takeda's Answer to Defendants/Counterclaimants Lupin's Counterclaims, U.S. District Court, District of Delaware, Case No. 14-CV-00184, *Teijin Limited* et al. vs. *Lupin Ltd.* et al. (Apr. 25, 2014).
First Amended Answer, Defenses and Counterclaims of Defendants Lupin Ltd. and Lupin Pharmaceuticals, Inc., U.S. District Court, District of Delaware, Case No. 14-CV-00184, *Teijin Limited* et al. vs. *Lupin Ltd.* et al. (May 7, 2014).
Complaint, U.S. District Court, District of Delaware, Case No. 13-1781, *Teijin Limited* et al. vs. *Mylan Pharmaceuticals Inc.* (Oct. 30, 2013).
Mylan Pharmaceuticals Inc.'s Answer to Complaint and Counterclaim Against Teijin Limited, Teijin Pharma Ltd. and Takeda Pharmaceuticals U.S.A., Inc., U.S. Distict Court, District of Delaware, Case No. 13-1781 (Nov. 27, 2013).
Mylan Pharmaceuticals Inc.'s Corrected Answer to Complaint and Counterclaim Against Teijin Limited, Teijin Pharma Ltd. and Takeda Pharmaceuticals U.S.A., Inc., U.S. Distict Court, District of Delaware, Case No. 13-1781 (Nov. 27, 2013).
Plaintiffs/Counterclaim Defendants Teijin Limited, Teijin Pharma Ltd. and Takeda Pharmaceuticals U.S.A., Inc.'s Reply to Defendant/Counterlcaimant Mylan Pharmaceuticals Inc.'s Counterclaims, U.S. Distict Court, District of Delaware, Case No. 13-1781 (Jan. 13, 2014).
Complaint, U.S. District Court, District of Delaware, Case No. 13-1780, *Teijin Limited* et al. vs. *Dr. Reddy's Laboratories Ltd.* et al. (Oct. 30, 2013).
Answer and Counterclaim of Dr. Reddy's Laboratories, Ltd. and Dr. Reddy's Laboratories, Inc., U.S. District Court, District of Delaware, Case No. 13-1780, *Teijin Limited* et al. vs. *Dr. Reddy's Laboratories Ltd.* et al. (Jan. 10, 2014).
Plaintiffs/Counterclaim Defendants Teijin Limited et al. Reply to Defendants/Counterclaimants Dr. Reddy's Laboratories, Inc. et al., Counterclaims, U.S. District Court, District of Delaware, Case No. 13-1780, *Teijin Limited* et al. vs. *Dr. Reddy's Laboratories Ltd.* et al. (Jan. 31, 2014).
Complaint, U.S. District Court, District of Delaware, Case No. 13-1852, *Teijin Limited* et al. vs. *Sun Pharma Global FZE* et al. (Nov. 6, 2013).
Sun Pharma Global FZE and Caraco Pharmaceutical Laboratories, Ltd.'s Answer and Defenses and Sun Pharma Global FZE's Counterclaims, U.S. District Court, District of Delaware, Case No. 13-1852, *Teijin Limited* et al. vs. *Sun Pharma Global FZE* et al. (Jan. 7, 2014).
Plaintiffs/Counterclaim Defendants Teijin Limited, Teijin Pharma Limited, and Takeda Pharmaceuticals U.S.A., Inc.'s Reply to Defendants/Counterclaimant Sun Pharma Global FZE Counterclaims, U.S. District Court, District of Delaware, Case No. 13-1852, *Teijin Limited* et al. vs. *Sun Pharma Global FZE* et al. (Jan. 31, 2014).
Complaint, U.S. District Court, District of Delaware, Case No. 13-1939, *Teijin Limited* et al. vs. *Alembic Pharmaceuticals Limited* (Nov. 19, 2013).
Defendant Alembic Pharmaceuticals Limited's Answer, Defenses and Counterclaims, U.S. District Court, District of Delaware, Case No. 13-1939, *Teijin Limited* et al. vs. *Alembic Pharmaceuticals Limited* (Jan. 17, 2014).
Plaintiff/Counterclaim Defendants Teijin Limited, Teijin Pharma Limited and Takeda Pharmaceuticals U.S.A., Inc. Answer to Defendant/Counterclaimant Alembic Pharmaceuticals Limited Counterclaims, U.S. District Court, District of Delaware, Case No. 13-1939, *Teijin Limited* et al. vs. *Alembic Pharmaceuticals Limited* (Feb. 10, 2014).
Complaint, U.S. District Court, District of Delaware, Case No. 14-0117, *Teijin Limited* et al. vs. *Ranbaxy Laboratories Limited* et al. (Jan. 31, 2014).
Defendants Ranbaxy Laboratories Limited, Ranbaxy Pharmaceuticals, Inc., and Ranbaxy Inc.'s Answer to Plaintiffs Complaint, U.S. District Court, District of Delaware, Case No. 14-0117, *Teijin Limited* et al. vs. *Ranbaxy Laboratories Limited* et al. (Feb. 26, 2014).
Complaint, U.S. District Court, District of Delaware, Case No. 14-0166, *Teijin Limited* et al. vs. *Hetero USA, Inc.* et al., (Feb. 7, 2014).
Defendants Hetero USA, Inc. and Hetero Labs Inc.'s Answer, Defenses and Counterclaims, U.S. District Court, District of Delaware, Case No. 14-0166, *Teijin Limited* et al. vs. *Hetero USA, Inc.* et al., (Apr. 2, 2014).
Plaintiffs/Counterclaim Defendants Teijin's and Takeda's Answer to Defendant/Counterclaimants Hetero's Counterclaims, U.S. District Court, District of Delaware, Case No. 14-0166, *Teijin Limited* et al. vs. *Hetero USA, Inc.* et al., (Apr. 28, 2014).
Complaint, U.S. District Court, District of Delaware, Case No. 14-0189, *Teijin Limited* et al. vs. *Roxane Laboratories, Inc.* (Feb. 12, 2014).
Defendant Roxane Laboratories, Inc.'s Answer and Affirmative Defenses to Plaintiffs Complaint, U.S. District Court, District of Delaware, Case No. 14-0189, *Teijin Limited* et al. vs. *Roxane Laboratories, Inc.* (Apr. 22, 2014).
Plaintiff/Counterclaim Defendants Teijin's and Takeda's Answer to Defendant/Counterclaimant Roxane's Counterclaims, U.S. District Court, District of Delaware, Case No. 14-0189, *Teijin Limited* et al. vs. *Roxane Laboratories, Inc.* (May 16, 2014).
Complaint, U.S. District Court, District of Delaware, Case No. 14-854, *Teijin Limited* et al. vs. *Prinston Pharmaceutical, Inc.* (Jul. 1, 2014).

(56) References Cited

OTHER PUBLICATIONS

Defendant Prinston Pharmaceutical, Inc.'s Answer, Defenses and Counterclaims, U.S. District Court, District of Delaware, Case No. 14-854, *Teijin Limited* et al. vs. *Prinston Pharmaceutical, Inc.* (Jul. 23, 2014).

Plaintiffs/Counterclaim Defendants Teijin's and Takeda's Answer to Defendant/Counterclaimant Prinston's Counterclaims, U.S. District Court, District of Delaware, Case No. 14-854, *Teijin Limited* et al. vs. *Prinston Pharmaceuticals, Inc.* (Aug. 7, 2014).

United States Patent Office Action for U.S. Appl. No. 12/689,266 dated Sep. 22, 2014 (11 pages).

United States Patent Office Action for U.S. Appl. No. 13/521,765 dated Oct. 22, 2014 (12 pages).

* cited by examiner

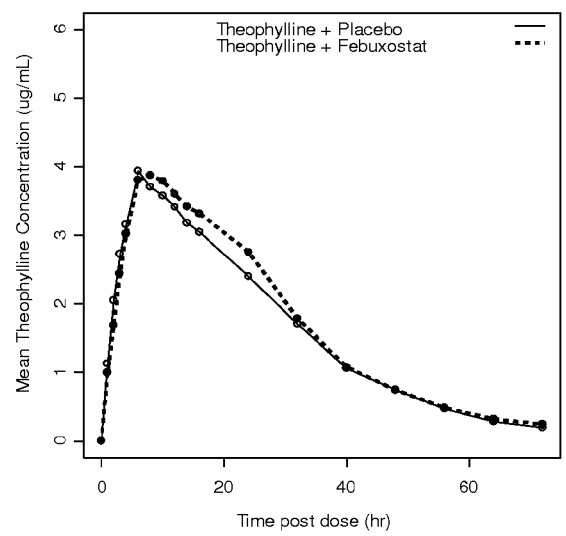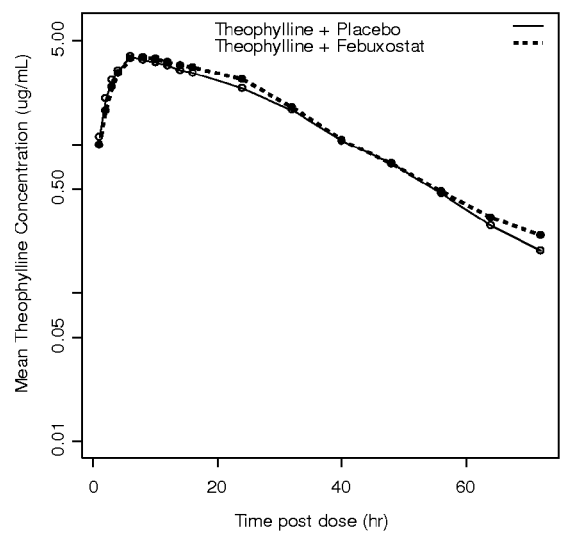

METHODS FOR CONCOMITANT TREATMENT OF THEOPHYLLINE AND FEBUXOSTAT

RELATED APPLICATION INFORMATION

This application claims priority to U.S. Provisional Patent Application No. 61/381,482 filed on Sep. 10, 2010, the contents of which are herein incorporated by reference in their entirety.

FIELD

The present disclosure relates to novel methods for treating hyperuricemia in patients also requiring treatment with theophylline. Specifically, the invention is directed to a method of administering theophylline in conjunction with one or more xanthine oxidoreductase inhibitors, whereby the xanthine oxidoreductase inhibitors do not cause alterations in the plasma concentrations of theophylline.

BACKGROUND

A substantial number of patients are affected with diseases of the respiratory system, including asthma, acute bronchitis, chronic bronchitis, emphysema, neonatal apnea, and neonatal bradycardia. One of the primary treatments for respiratory diseases is the use of theophylline.

Theophylline is a useful medicine frequently used as an agent for treating symptoms of bronchial asthma. It is known in the art that effective blood concentrations range from about 10 to 20 μg/ml. However, if the concentration of theophylline in the blood exceeds 20 μg/ml, serious side effects sometimes appear with regard to the cardiovascular system and the central nervous system. Further, there is a large difference in blood levels among individuals. Various conditions (e.g., cardiac insufficiency, liver and kidney disease, etc.), age differences, smoking, etc. also have large effects. Additionally, theophylline has a short biological half-life of about 6 hours for adults. In order to maintain the effective blood level, four doses per day have been considered necessary. However, such frequent dosing is troublesome to patients, reduces patient compliance, and causes the state of the disease to become worse. In particular, attacks of bronchial asthma often occur at daybreak. It is not possible to sufficiently prevent such attacks with ingestion of theophylline just before going to bed, and therefore, repeat ingestion close to daybreak is necessary. Thus, in the past, continuous effort has been made to develop a sustained release type theophylline formulation. Several formulations are already available on the market.

Another disease that affects a substantial number of patients is gout. Gout affects 3 to 5 million individuals in the United States of America (USA) and is increasing in incidence and prevalence. Gout is a serious health condition characterized by flares of acute arthritis, chronic gouty arthropathy, tophi, and uric acid urolithiasis, and is associated with a broad range of comorbidities, including cardiovascular disease, chronic kidney disease, and metabolic syndrome. At the joint level, a gout flare is best characterized as an acute monoarthritis arthropathy process with proliferative bone reaction that can affect any joint and that can later develop into chronic polyarthritis. Gout attacks tend to occur mostly in the lower extremities and over time additional joints can be involved.

The underlying metabolic aberration in gout is hyperuricemia, which is a condition defined as an elevation in serum urate (sUA) level ≥6.8 m/dL. Hyperuricemia develops into gout when urate crystals are formed from supersaturated body fluids and deposited in joints, tophi, and parenchymal organs due to a disorder in the urate metabolism. Uric acid is the end product of purine metabolism and is generated in the cascade of hypoxanthine→xanthine→uric acid.

Urate-lowering therapy (ULT) is used to treat hyperuricemia in subjects with gout. The goal of ULT is to reduce sUA to 6.0 mg/dL or less, below the concentration at which monosodium urate saturates extracellular fluid. Using ULT to reduce and maintain sUA levels <6.0 mg/dL ultimately improves the clinical symptoms of gout by reducing the frequency of gout flares, decreasing size and number of tophi, and improving quality of life. One alternative that may be used for the treatment of gout is the administration of xanthine oxidase inhibitors, such as allopurinol. Generally, allopurinol is considered one of the primary treatments of gout and has developed wide usage as a treatment for gout.

However, clinicians have few treatment options for hyperuricemic patients also suffering from respiratory diseases, such as chronic obstructive pulmonary disease, asthma, acute bronchitis, chronic bronchitis, emphysema, neonatal apnea, and neonatal bradycardia. One of the primary treatments for these respiratory diseases is the administration of theophylline, a bronchodilator. Although theophylline provides a treatment for the respiratory diseases described herein, the therapeutic range of theophylline blood concentrations is thought to be very narrow, ranging from about 10 to about 20 μg/ml. As such, if the theophylline dosing does not provide a minimum blood concentration of 10 μg/ml, the patient is not provided significant relief from the respiratory condition, and at blood concentrations greater than 20 μg/ml, the patient may be susceptible to adverse effects such as abdominal pain, headache, muscle cramps, tremors, tachycardia, and seizures. Therefore, clinicians must exercise caution in determining treatment options for patients requiring theophylline treatment, and must closely monitor the potential for drug interactions that may increase or decrease theophylline blood concentrations.

It is further known within the art that the administration of allopurinol interacts with the metabolism of theophylline, causing the theophylline to be metabolized slowly, and leading to increased blood concentrations. As discussed in the art, the area under the curve (AUC) for theophylline in patients co-administered allopurinol and theophylline has been reported to increase by up to 27%, the half-life increased by approximately 25%, and the clearance of theophylline may be decreased by 21% (Manfredi B A, et al., *Clin. Pharmacol. Ther.*, 1981; 29(2), pp. 224-229). Accordingly, clinicians are required to alter the theophylline dosing and/or the allopurinol dosing in hopes of establishing a therapeutic dose for both disease states, while avoiding unwanted adverse effects that may result from increased theophylline concentrations.

Thus, in view of these considerations, there exists within the art a need to develop a treatment option for hyperuricemic patients that also suffer from respiratory disorders, whereby the clinician can administer typical dosing of theophylline without adjusting for adverse drug interactions.

SUMMARY

The present disclosure is directed to methods for treating hyperuricemia in patients requiring treatment with theophylline. The methods of the current invention avoid the drug interactions typically associated with theophylline administration and concomitant treatment with xanthine oxidase inhibitors.

In one embodiment, the present disclosure provides a method of treating hyperuricemia in a patient in need of treatment thereof, the method comprising the steps of: administering to the patient suffering from hyperuricemia and at least one secondary disease state, a therapeutically effective amount of at least one xanthine oxidoreductase inhibitor, wherein said subject is also receiving a concomitant administration of theophylline to treat the at least one secondary disease state; and further wherein (i) the administration of the at least one xanthine oxidoreductase inhibitor to said patient does not result in theophylline toxicity to said patient; and (ii) administration of the theophylline is in an amount ranging from about 90% to about 110% of a manufacturer's recommended theophylline dosage amount in the absence of administration of at least one xanthine oxidoreductase inhibitor.

The secondary disease state may include asthma, acute bronchitis, chronic bronchitis, emphysema, neonatal apnea, neonatal bradycardia, and combinations thereof. As described in the method of this embodiment, the xanthine oxidoreductase inhibitor may include 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±), 3-(2-methyl-4-pyridyl)-5-cyano-4-isobutoxyphenyl)-1,2,4-triazole and pharmaceutically acceptable salts thereof.

Moreover, the method of the current embodiment may include a theophylline dose ranging from about 95% to about 105%, and from about 99% to about 101% of a manufacturer's recommended theophylline dosage amount in the absence of administration of at least one xanthine oxidoreductase inhibitor. The method of the current invention may also include patients suffering from a third disease state, including gout, hypertension, renal failure, nephrolithiasis, acute gouty arthritis, chronic gouty joint disease, tophaceous gout, uric acid urolithiasis, uric acid nephropathy, progressive renal disease, and combinations thereof. Further, the methods of the current embodiment include the treatment of hyperuricemia in patients that were previously receiving theophylline treatment prior to treatment with a xanthine oxidoreductase inhibitor.

In another embodiment, the current invention provides a method of treating hyperuricemia in a patient in need of treatment thereof, the method comprising the steps of: administering to the patient suffering from hyperuricemia and at least one second disease state, a therapeutically effective amount of at least one xanthine oxidoreductase inhibitor, wherein said subject will also be receiving a concomitant administration of theophylline to treat at least one second disease state, and further wherein (i) the administration of the at least one xanthine oxidoreductase inhibitor to said patient will not result in theophylline toxicity to said patient; and (ii) administration of the theophylline will be in an amount ranging from about 90% to about 110% of a manufacturer's recommended theophylline dosage amount in the absence of administration of at least one xanthine oxidoreductase inhibitor.

The secondary disease state may include asthma, acute bronchitis, chronic bronchitis, emphysema, neonatal apnea, neonatal bradycardia, and combinations thereof. As described in the method of this embodiment, the xanthine oxidoreductase inhibitor may include 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±), 3-(2-methyl-4-pyridyl)-5-cyano-4-isobutoxyphenyl)-1,2,4-triazole and pharmaceutically acceptable salts thereof.

Moreover, the method of the current embodiment may include a theophylline dose ranging from about 95% to about 105%, and from about 99% to about 101% of a manufacturer's recommended theophylline dosage amount in the absence of administration of at least one xanthine oxidoreductase inhibitor. The method of the current invention may also include patients suffering from a third disease state, including gout, hypertension, renal failure, nephrolithiasis, acute gouty arthritis, chronic gouty joint disease, tophaceous gout, uric acid urolithiasis, uric acid nephropathy, progressive renal disease, and combinations thereof. Further, the methods of the current embodiment include the treatment of hyperuricemia in patients that have not previously received theophylline treatment prior to treatment with a xanthine oxidoreductase inhibitor, and will begin treatment with both medications concurrently.

In yet another embodiment, the present disclosure provides a method of treating hyperuricemia in a patient suffering from gout and in need of treatment thereof, the method comprising the steps of: administering to the patient suffering from gout and hyperuricemia and at least one third disease state, a therapeutically effective amount of at least one xanthine oxidoreductase inhibitor, wherein said subject is also receiving a concomitant administration of theophylline to treat the at least one third disease state; and further wherein (i) the administration of the at least one xanthine oxidoreductase inhibitor to said patient does not result in theophylline toxicity to said patient; and (ii) administration of the theophylline is in an amount ranging from about 90% to about 110% of a manufacturer's recommended theophylline dosage amount in the absence of administration of at least one xanthine oxidoreductase inhibitor.

The third disease state may include asthma, acute bronchitis, chronic bronchitis, emphysema, neonatal apnea, neonatal bradycardia, and combinations thereof. As described in the method of this embodiment, the xanthine oxidoreductase inhibitor may include 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±), 3-(2-methyl-4-pyridyl)-5-cyano-4-isobutoxyphenyl)-1,2,4-triazole and pharmaceutically acceptable salts thereof.

Moreover, the method of the current embodiment may include a theophylline dose ranging from about 95% to about 105%, and from about 99% to about 101% of a manufacturer's recommended theophylline dosage amount in the absence of administration of at least one xanthine oxidoreductase inhibitor. The method of the current invention may also include patients suffering from a fourth disease state, including hypertension, renal failure, nephrolithiasis, acute gouty arthritis, chronic gouty joint disease, tophaceous gout, uric acid urolithiasis, uric acid nephropathy, progressive renal disease, and combinations thereof. Further, the methods of the current embodiment include the treatment of hyperuricemia in patients suffering from gout and that were previously receiving theophylline treatment prior to treatment with a xanthine oxidoreductase inhibitor.

In another embodiment, the current invention provides a method of treating hyperuricemia in a patient suffering from gout and in need of treatment thereof, the method comprising the steps of: administering to the patient suffering from gout and hyperuricemia and at least one third disease state, a therapeutically effective amount of at least one xanthine oxidoreductase inhibitor, wherein said subject will also be receiving a concomitant administration of theophylline to treat at least one third disease state, and further wherein (i) the administration of the at least one xanthine oxidoreductase inhibitor to said patient will not result in theophylline toxicity to said patient; and (ii) administration of the theophylline will be in an amount ranging from about 90% to about 110% of a manufacturer's recommended theophylline dosage amount in the absence of administration of at least one xanthine oxidoreductase inhibitor.

The third disease state may include asthma, acute bronchitis, chronic bronchitis, emphysema, neonatal apnea, neonatal bradycardia, and combinations thereof. As described in the method of this embodiment, the xanthine oxidoreductase inhibitor may include 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±), 3-(2-methyl-4-pyridyl)-5-cyano-4-isobutoxyphenyl)-1,2,4-triazole and pharmaceutically acceptable salts thereof.

Moreover, the method of the current embodiment may include a theophylline dose ranging from about 95% to about 105%, and from about 99% to about 101% of a manufacturer's recommended theophylline dosage amount in the absence of administration of at least one xanthine oxidoreductase inhibitor. The method of the current invention may also include patients suffering from a fourth disease state, including hypertension, renal failure, nephrolithiasis, acute gouty arthritis, chronic gouty joint disease, tophaceous gout, uric acid urolithiasis, uric acid nephropathy, progressive renal disease, and combinations thereof. Further, the methods of the current embodiment include the treatment of hyperuricemia in patients that have not previously received theophylline treatment prior to treatment with a xanthine oxidoreductase inhibitor, and will begin treatment with both medications concurrently.

In still yet another embodiment, the present disclosure provides a method of treating a patient in need of treatment thereof, the method comprising the steps of: administering to the patient suffering from at least one first disease state and at least one secondary disease state, a therapeutically effective amount of at least one xanthine oxidoreductase inhibitor, wherein said subject is also receiving a concomitant administration of theophylline to treat the at least one secondary disease state; and further wherein (i) the administration of the at least one xanthine oxidoreductase inhibitor to said patient does not result in theophylline toxicity to said patient; and (ii) administration of the theophylline is in an amount ranging from about 90% to about 110% of a manufacturer's recommended theophylline dosage amount in the absence of administration of at least one xanthine oxidoreductase inhibitor.

The first disease state may include gout, prostatitis, inflammatory bowel disease, QT interval prolongation, myocardial infarction, cardiac hypertrophy, hypertension, nephrolithiasis, renal impairment, chronic kidney disease, metabolic syndrome, diabetes, diabetic nephropathy, congestive heart failure and combinations thereof.

The secondary disease state may include asthma, acute bronchitis, chronic bronchitis, emphysema, neonatal apnea, neonatal bradycardia, and combinations thereof. As described in the method of this embodiment, the xanthine oxidoreductase inhibitor may include 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±), 3-(2-methyl-4-pyridyl)-5-cyano-4-isobutoxyphenyl)-1,2,4-triazole and pharmaceutically acceptable salts thereof.

Moreover, the method of the current embodiment may include a theophylline dose ranging from about 95% to about 105%, and from about 99% to about 101% of a manufacturer's recommended theophylline dosage amount in the absence of administration of at least one xanthine oxidoreductase inhibitor. The method of the current invention may also include patients suffering from a third disease state, including gout, hypertension, renal failure, nephrolithiasis, acute gouty arthritis, chronic gouty joint disease, tophaceous gout, uric acid urolithiasis, uric acid nephropathy, progressive renal disease, and combinations thereof. Further, the methods of the current embodiment include the treatment of the first disease state in patients that were previously receiving theophylline treatment prior to treatment with a xanthine oxidoreductase inhibitor.

BRIEF DESCRIPTION OF THE FIGURE

FIG. 1 shows the mean theophylline plasma concentration-time profiles following an oral dose of 400 mg theophylline coadministered with 80 mg of 2-[3-cyano-4-(2-methylpropoxy)phenyl]-4-methylthiazole-5-carboxylic acid (also known as "febuxostat") or matching placebo as described in Example 1.

DETAILED DESCRIPTION OF THE DISCLOSURE

I. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such dosages are thus encompassed by the scope of the claims reciting the terms "about" and "approximately."

As used herein, the term "AUC" refers to the area under the plasma concentration time curve of the active agent and which is calculated using the trapezoidal rule. The term "$AUC_t$," means the area under the plasma concentration time curve from time 0 to 120 hours after administration in units of ng·h/mL as determined using the trapezoidal rule. The term "AUC∞" means the area under the plasma concentration time curve from time 0 to infinite time. AUC∞ is calculated as $AUC_t$+LMT/(-β), where "LMT" is the last measurable plasma concentration and β is the terminal phase elimination rate constant. Unless otherwise noted herein, the reported value for the AUC is the central value of the AUC. The "central value" of the AUC is the mean AUC±standard deviation.

The terms "administer", "administering", "administered" or "administration" refer to any manner of providing a drug (such as, a xanthine oxidoreductase inhibitor or a pharmaceutically acceptable salt thereof) to a subject or patient. Routes of administration can be accomplished through any means known by those skilled in the art. Such means include, but are not limited to, oral, buccal, intravenous, subcutaneous, intramuscular, transdermal, by inhalation and the like.

The term "active agent" as used herein refers to (1) a xanthine oxidoreductase inhibitor or a pharmaceutically acceptable salt thereof or (2) a xanthine oxidase inhibitor or a pharmaceutically acceptable salt thereof. The term "active agent" and "drug" are used interchangeably herein. The solid state form of the active agent used in preparing the dosage forms of the present disclosure is not critical. For example, active agent used in preparing the modified release dosage forms of the present disclosure can be amorphous or crystalline. The final dosage form contains at least a detectable amount of crystalline active agent. The crystalline nature of the active agent can be detected using powder X-ray diffraction analysis, by differential scanning calorimetry or any other techniques known in the art.

The term "$C_{max}$" refers to the maximum observed plasma concentration of a xanthine oxidoreductase inhibitor or salt thereof produced by the ingestion of the dosage forms of the present disclosure. Unless otherwise noted herein, the reported value for the $C_{max}$ is the central value of the $C_{max}$. The "central value" of the $C_{max}$ is the mean $C_{max}$±standard deviation.

The term "dosage form" refers to any solid object, semi-solid, or liquid composition designed to contain a specific pre-determined amount (i.e., dose) of a certain active agent. Suitable dosage forms may be pharmaceutical drug delivery systems, including those for oral administration, buccal administration, rectal administration, topical or mucosal delivery or subcutaneous implants, or other implanted drug delivery systems and the like. In one aspect, the dosage forms of the present disclosure are considered to be solid, however, they may contain liquid or semi-solid components. In another apsect, the dosage form is an orally administered system for delivering an active agent to the gastrointestinal tract of a subject. The dosage form of the present disclosure exhibit modified release of the active agent.

By an "effective amount" or a "therapeutically effective amount" of an active agent is meant a nontoxic but sufficient amount of the active agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective amount" in any individual case may be determined by one of ordinary skill in the art using routine experimentation. For example, the daily therapeutically effective or prophylactically effective amount of xanthine oxidoreductase inhibiting compounds administered to a patient in single or divided doses range from about 0.01 to about 750 milligram per kilogram of body weight per day (mg/kg/day). More specifically, a patient may be administered from about 5.0 mg to about 300 mg once daily, from about 20 mg to about 240 mg once daily and from about 40 mg to about 120 mg once daily of xanthine oxidoreductase inhibiting compounds. Of course, it will be understood by one skilled in the art that other dosage regimens may be utilized, such as dosing more than once per day, utilizing extended, controlled, or modified release dosage forms, and the like in order to achieve the desired result.

By "pharmaceutically acceptable," such as in the recitation of a "pharmaceutically acceptable excipient," or a "pharmaceutically acceptable additive," is meant a material that is not biologically or otherwise undesirable, i.e., the material may be incorporated into a pharmaceutical composition administered to a patient without causing any undesirable biological effects.

The term "subject" refers to an animal. In one aspect, the animal is a mammal, including a human or non-human. The terms patient and subject may be used interchangeably herein.

The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

As used herein, the term "xanthine oxidoreductase" refers to at least one form of xanthine oxidoreductase enzyme, namely xanthine oxidase and/or xanthine dehydrogenase.

As used herein, the phrase "xanthine oxidoreductase inhibitor" refers to any compound that (1) is an inhibitor of a xanthine oxidoreductase, such as, but not limited to, xanthine oxidase; and (2) chemically, does not contain a purine ring in its structure (i.e. is a "non-purine" analogue). The phrase "xanthine oxidoreductase inhibitor" as defined herein also includes metabolites, polymorphs, solvates and prodrugs of such compounds, including metabolites, polymorphs, solvates and prodrugs of the exemplary compounds described as Formula I and Formula II below. Examples of xanthine oxidoreductase inhibitors include, but are not limited to, 2-[4-(2-carboxypropoxy)-3-cyanophenyl]-4-methyl-5-thiazole-carboxylic acid and compounds having the following Formula I or Formula II:

Compounds of Formula I:

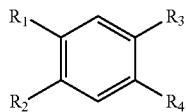

wherein $R_1$ and $R_2$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, a phenylsulfinyl group or a cyano (—CN) group;

wherein $R_3$ and $R_4$ are each independently a hydrogen or A, B, C or D as shown below:

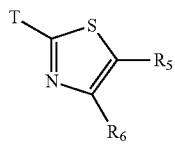   A

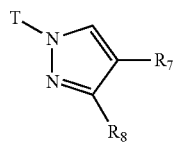   B

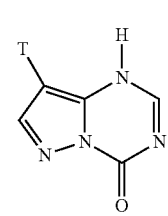   C

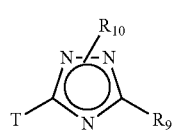   D wherein T connects or attaches A, B, C or D to the aromatic ring shown above at $R_1$, $R_2$, $R_3$ or $R_4$.

wherein $R_5$ and $R_6$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_7$ and $R_8$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_9$ is an unsubstituted pyridyl group or a substituted pyridyl group; and wherein $R_{10}$ is a hydrogen or a lower alkyl group, a lower alkyl group substituted with a pivaloyloxy group and in each case, $R_{10}$ bonds to one of the nitrogen atoms in the 1,2,4-triazole ring shown above in Formula I.

Compounds of Formula II:

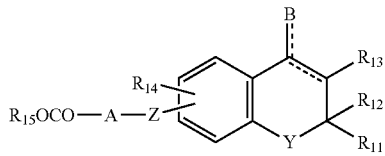

wherein $R_{11}$ and $R_{12}$ are each independently a hydrogen, a substituted or unsubstituted lower alkyl group, a substituted or unsubstituted phenyl (the substituted phenyl in this Formula II refers to a phenyl substituted with a halogen or lower alkyl, and the like. Examples include, but are not limited to, p-tolyl and p-chlorophenyl), or $R_{11}$ and $R_{12}$ may together form a four- to eight-membered carbon ring together with the carbon atom to which they are attached;

wherein $R_{13}$ is a hydrogen or a substituted or unsubstituted lower alkyl group;

wherein $R_{14}$ is one or two radicals selected from a group consisting of a hydrogen, a halogen, a nitro group, a substituted or unsubstituted lower alkyl group, a substituted or unsubstituted phenyl (the substituted phenyl in this Formula II refers to a phenyl substituted with a halogen or lower alkyl group, and the like. Examples include, but are not limited to, p-tolyl and p-chlorophenyl), —$OR_{16}$ and —$SO_2NR_{17}R_{17'}$, wherein $R_{16}$ is a hydrogen, a substituted or unsubstituted lower alkyl, a phenyl-substituted lower alkyl, a carboxymethyl or ester thereof, a hydroxyethyl or ether thereof, or an allyl; $R_{17}$ and $R_{17'}$ are each independently a hydrogen or a substituted or unsubstituted lower alkyl group;

wherein $R_{15}$ is a hydrogen or a pharmaceutically active ester-forming group;

wherein A is a straight or branched hydrocarbon radical having one to five carbon atoms;

wherein B is a halogen, an oxygen, or an ethylenedithio;

wherein Y is an oxygen, a sulfur, a nitrogen or a substituted nitrogen;

wherein Z is an oxygen, a nitrogen or a substituted nitrogen; and the dotted line refers to either a single bond, a double bond, or two single bonds (for example, when B is ethylenedithio, the dotted line shown in the ring structure can be two single bonds).

As used herein, the term "lower alkyl(s)" group refers to a $C_1$-$C_7$ alkyl group, including, but not limited to, including methyl, ethyl, n-propyl, isopropyl, butyl, isobutyl, sec-butyl, tert-butyl, pentyl, isopentyl, hexyl, heptal and the like.

As used herein, the term "lower alkoxy" refers to those groups formed by the bonding of a lower alkyl group to an oxygen atom, including, but not limited to, methoxy, ethoxy, propoxy, isopropoxy, butoxy, isobutoxy, pentoxy, hexoxy, heptoxy and the like.

As used herein, the term "lower alkylthio group" refers to those groups formed by the bonding of a lower alkyl to a sulfur atom.

As used herein, the term "halogen" refers to fluorine, chlorine, bromine and iodine.

As used herein, the term "substituted pyridyl" refers to a pyridyl group that can be substituted with a halogen, a cyano group, a lower alkyl, a lower alkoxy or a lower alkylthio group.

As used herein, the term "four- to eight-membered carbon ring" refers to cyclobutyl, cyclopentyl, cyclohexyl, cycloheptyl, cyclooctyl and the like.

As used herein, the phrase "pharmaceutically active ester-forming group" refers to a group which binds to a carboxyl group through an ester bond. Such ester-forming groups can be selected from carboxy-protecting groups commonly used for the preparation of pharmaceutically active substances, especially prodrugs. For the purpose of the present disclosure, said group should be selected from those capable of binding to compounds having Formula II wherein $R_{15}$ is hydrogen through an ester bond. Resultant esters are effective to increase the stability, solubility, and absorption in gastrointestinal tract of the corresponding non-esterified forms of said compounds having Formula II, and also prolong the effective blood-level of it. Additionally, the ester bond can be cleaved easily at the pH of body fluid or by enzymatic actions in vivo to provide a biologically active form of the compound having Formula II. Preferred pharmaceutically active ester-forming groups include, but are not limited to, 1-(oxygen substituted)-$C_2$ to $C_{15}$ alkyl groups, for example, a straight, branched, ringed, or partially ringed alkanoyloxyalkyl groups, such as acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl, and the like, $C_3$ to $C_{15}$ alkoxycarbonyloxyalkyl groups, such as ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexyl methoxycarbonyloxyethyl, bornyloxycarbonyloxyisopropyl, and the like, $C_2$ to $C_8$ alkoxyalkyls, such as methoxy methyl, methoxy ethyl, and the like, $C_4$ to $C_8$ 2-oxacycloalkyls such as, tetrahydropyranyl, tetrahydrofuranyl, and the like, substituted $C_8$ to $C_{12}$ aralkyls, for example, phenacyl, phthalidyl, and the like, $C_6$ to $C_{12}$ aryl, for example, phenyl xylyl, indanyl, and the like, $C_2$ to $C_{12}$ alkenyl, for example, allyl, (2-oxo-1,3-dioxolyl)methyl, and the like, and [4,5-dihydro-4-oxo-1H-pyrazolo[3,4-d]pyrimidin-1-yl]methyl, and the like.

In $R_{16}$ in Formula II, the term "ester" as used in the phrase "the ester of carboxymethyl" refers to a lower alkyl ester, such as methyl or ethyl ester; and the term "ether" used in the phrase "the ether of hydroxyethyl" means an ether which is formed by substitution of the hydrogen atom of hydroxyl group in the hydroxyethyl group by aliphatic or aromatic alkyl group, such as benzyl.

The carboxy-protecting groups may be substituted in various ways. Examples of substituents include halogen atom, alkyl groups, alkoxy groups, alkylthio groups and carboxy groups.

As used herein, the term "straight or branched hydrocarbon radical" in the definition of A in Formula II above refers to methylene, ethylene, propylene, methylmethylene, or isopropylene.

As used herein, the substituent of the "substituted nitrogen" in the definition of Y and Z in Formula II above are hydrogen, lower alkyl, or acyl.

As used herein, the term "phenyl-substituted lower alkyl" refers to a lower alkyl group substituted with phenyl, such as benzyl, phenethyl or phenylpropyl. As used herein, the term "prodrug" refers to a derivative of the compounds shown in the above-described Formula I and Formula II that have chemically or metabolically cleavable groups and become by solvolysis or under physiological conditions compounds that are pharmaceutically active in vivo. Esters of carboxylic acids are an example of prodrugs that can be used in the dosage forms of the present disclosure. Methyl ester prodrugs may be prepared by reaction of a compound having the above-described formula in a medium such as methanol with an acid or base esterification catalyst (e.g., NaOH, $H_2SO_4$). Ethyl ester prodrugs are prepared in similar fashion using ethanol in place of methanol.

Examples of compounds having the above Formula I are: 2-[3-cyano-4-(2-methylpropoxy)phenyl]-4-methylthiazole-5-carboxylic acid (also known as "febuxostat"), 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±) or 3-(2-methyl-4-pyridyl)-5-cyano-4-isobutoxyphenyl)-1,2,4-triazole.

Preferred compounds having the above Formula I are: 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid. These preferred compounds have also been found not have an effect at a therapeutically effective amount in a subject on the activity of any of the following enzymes involved in purine and pyrimidine metabolism: guanine deaminase, hypoxanthine-guanine phosphoribosyltransferse, purine nucleotide phosphorylase, orotate phosphoribosyltransferase or orotidine-5-monophosphate decarboxylase (i.e., meaning that it is "selective" for none of these enzymes which are involved in purine and pyrimidine metabolism). Assays for determining the activity for each of the above-described enzymes is described in Yasuhiro Takano, et al., *Life Sciences,* 76:1835-1847 (2005). These preferred compounds have also been referred to in the literature as nonpurine, selective inhibitors of xanthine oxidase (NP/SIXO).

Examples of compounds having the above Formula II are described in U.S. Pat. No. 5,268,386 and EP 0 415 566 A1, and are incorporated, in their entirety, herein.

With the exception of pyrazolo[1,5-a]-1,3,5-triazin-4-(1H)-one, 8-[3-methoxy-4-(phenylsulfinyl)phenyl]-sodium salt (±), methods for making xanthine oxidoreductase inhibiting compounds of Formulas I and II for use in the methods of the present disclosure are known in the art and are described, for example, in U.S. Pat. Nos. 5,268,386, 5,614,520, 6,225,474, 7,074,816 and EP 0 415 566 A1 and in the publications Ishibuchi, S. et al., *Bioorg. Med. Chem. Lett.*, 11:879-882 (2001) and which are each herein incorporated by reference. Other xanthine oxidoreductase inhibiting compounds can be found using xanthine oxidoreductase and xanthine in assays to determine if such candidate compounds inhibit conversion of xanthine into uric acid. Such assays are well known in the art.

Pyrazolo[1,5-a]-1,3,5-triazin-4-(1H)-one, 8-[3-methoxy-4-(phenylsulfinyl)phenyl]-sodium salt (±) is available from Otsuka Pharmaceutical Co. Ltd. (Tokyo, Japan) and is described in the following publications: Uematsu T., et al., "Pharmacokinetic and Pharmacodynamic Properties of a Novel Xanthine Oxidase Inhibitor, BOF-4272, in Healthy Volunteers, *J. Pharmacology and Experimental Therapeutics,* 270:453-459 (August 1994), Sato, S., A Novel Xanthine Deydrogenase Inhibitor (BOF-4272). *In Purine and Pyrimidine Metabolism in Man,* Vol. VII, Part A, ed. By P. A. Harkness, pp. 135-138, Plenum Press, New York. Pyrazolo[1,5-a]-1,3,5-triazin-4-(1H)-one, 8-[3-methoxy-4-(phenylsulfinyl)phenyl]-sodium salt (±) can be made using routine techniques known in the art.

II. Methods of Treatment

The present disclosure relates to methods of treating hyperuricemia in patients that also require treatment with theophylline, without having to adjust the theophylline dose to account for the hyperuricemia treatment. Specifically, the present disclosure provides in one aspect, a method of treating hyperuricemia in a patient in need of treatment thereof, the method comprising the step of: administering to a patient suffering from hyperuricemia and at least one secondary disease state, a therapeutically effective amount of at least one xanthine oxidoreductase inhibitor, wherein said subject is also receiving a concomitant administration of theophylline to treat the at least one second disease state, and further wherein (i) the administration of the at least one xanthine oxidoreductase inhibitor to said patient does not result in theophylline toxicity to said patient; and (ii) administration of the theophylline is in an amount ranging from about 90% to about 110% of a manufacturer's recommended theophylline dosage amount in the absence of administration of at least one xanthine oxidoreductase inhibitor. More specifically, administration of the theophylline can be in an amount ranging from about 91% to about 109%, about 91% to about 108%, about 91% to about 107%, about 91% to about 106%, about 91% to about 105%, about 91% to about 104%, about 91% to about 103%, about 91% to about 102%, about 91% to about 101%, about 92% to about 109%, about 92% to about 108%, about 92% to about 107%, about 92% to about 106%, about 92% to about 105%, about 92% to about 104%, about 92% to about 103%, about 92% to about 102%, about 92% to about 101%, about 93% to about 109%, about 93% to about 108%, about 93% to about 107%, about 93% to about 106%, about 93% to about 105%, about 93% to about 104%, about 93% to about 103%, about 93% to about 102%, about 93% to about 101%, about 94% to about 109%, about 94% to about 108%, about 94% to about 107%, about 94% to about 106%, about 94% to about 105%, about 94% to about 104%, about 94% to about 103%, about 94% to about 102%, about 94% to about 101%, about 95% to about 109%, about 95% to about 108%, about 95% to about 107%, about 95% to about 106%, about 95% to about 105%, about 95% to about 104%, about 95% to about 103%, about 95% to about 102%, about 95% to about 101%, about 96% to about 109%, about 96% to about 108%, about 96% to about 107%, about 96% to about 106%, about 96% to about 105%, about 96% to about 104%, about 96% to about 103%, about 96% to about 102%, about 96% to about 101%, about 97% to about 109%, about 97% to about 108%, about 97% to about 107%, about 97% to about 106%, about 97% to about 105%, about 97% to about 104%, about 97% to about 103%, about 97% to about 102%, about 97% to about 101%, about 98% to about 109%, about 98% to about 108%, about 98% to about 107%, about 98% to about 106%, about 98% to about 105%, about 98% to about 104%, about 98% to about 103%, about 98% to about 102%, about 98% to about 101%, about 99% to about 109%, about 99% to about 108%, about 99% to about 107%, about 99% to about 106%, about 99% to about 105%, about 99% to about 104%, about 99% to about 103%, about 99% to about 102% or about 99% to about 101% of a manufacturer's recommended theophylline dosage amount in the absence of administration of at least one xanthine oxidoreductase inhibitor.

In another aspect, the present disclosure provides a method of treating hyperuricemia in a patient in need of treatment thereof, the method comprising the step of: administering to a patient suffering from hyperuricemia and at least one secondary disease state, a therapeutically effective amount of at least one xanthine oxidoreductase inhibitor, wherein said subject will also be receiving a concomitant administration of theophylline ("will also be receiving" meaning such as, concurrently with the xanthine oxidoreductase inhibitor, or subsequent to the initiation of treatment with the xanthine oxidoreductase inhibitor) to treat the at least one second disease state, and further wherein (i) the administration of the at least one xanthine oxidoreductase inhibitor to said patient does not result in theophylline toxicity to said patient; and (ii) administration of the theophylline is in an amount ranging from about 90% to about 110% of a manufacturer's recommended theophylline dosage amount in the absence of administration of at least one xanthine oxidoreductase inhibitor. More specifically, administration of the theophylline can be in an amount ranging from about 91% to about 109%, about 91% to about 108%, about 91% to about 107%, about 91% to about 106%, about 91% to about 105%, about 91% to about 104%, about 91% to about 103%, about 91% to about 102%, about 91% to about 101%, about 92% to about 109%, about 92% to about 108%, about 92% to about 107%, about 92% to about 106%, about 92% to about 105%, about 92% to about 104%, about 92% to about 103%, about 92% to about 102%, about 92% to about 101%, about 93% to about 109%, about 93% to about 108%, about 93% to about 107%, about 93% to about 106%, about 93% to about 105%, about 93% to about 104%, about 93% to about 103%, about 93% to about 102%, about 93% to about 101%, about 94% to about 109%, about 94% to about 108%, about 94% to about 107%, about 94% to about 106%, about 94% to about 105%, about 94% to about 104%, about 94% to about 103%, about 94% to about 102%, about 94% to about 101%, about 95% to about 109%, about 95% to about 108%, about 95% to about 107%, about 95% to about 106%, about 95% to about 105%, about 95% to about 104%, about 95% to about 103%, about 95% to about 102%, about 95% to about 101%, about 96% to about 109%, about 96% to about 108%, about 96% to about 107%, about 96% to about 106%, about 96% to about 105%, about 96% to about 104%, about 96% to about 103%, about 96% to about 102%, about 96% to about 101%, about 97% to about 109%, about 97% to about 108%, about 97% to about 107%, about 97% to about 106%, about 97% to about 105%, about 97% to about 104%, about 97% to about 103%, about 97% to about 102%, about 97% to about 101%, about 98% to about 109%, about 98% to about 108%, about 98% to about 107%, about 98% to about 106%, about 98% to about 105%, about 98% to about 104%, about 98% to about 103%, about 98% to about 102%, about 98% to about 101%, about 99% to about 109%, about 99% to about 108%, about 99% to about 107%, about 99% to about 106%, about 99% to about 105%, about 99% to about 104%, about 99% to about 103%, about 99% to about 102% or about 99% to about 101% of a manufacturer's recommended theophylline dosage amount in the absence of administration of at least one xanthine oxidoreductase inhibitor.

The method of the current invention comprises the co-administration of a xanthine oxidoreductase inhibitor and theophylline. The term xanthine oxidoreductase includes multiple therapeutic compounds, which have been described previously, and which are incorporated in their entirety herein. Generally, xanthine oxidoreductase inhibitors are compounds that inhibit the activity of xanthine oxidase, an enzyme involved in purine metabolism. In humans, inhibition of xanthine oxidase reduces the production of uric acid, which leads to secondary disease states such as gout, and other related diseases. Xanthine oxidoreductase inhibitors typically are classified as one of two types: purine analogues and non-purine analogues. The xanthine oxidoreductase inhibitors of the current invention include non-purine analogues, and, as noted previously, lack a purine ring in its chemical structure. In one embodiment, the xanthine oxidoreductase inhibitor includes, but is not limited to 2-[3-cyano-4-(2-methylpropoxy)phenyl]-4-methylthiazole-5-carboxylic acid (also known as "febuxostat"), 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo[1,5-a]-1,3,5-triazin-4-(1H)-one, 8-[3-methoxy-4-(phenylsulfinyl)phenyl]-sodium salt (±) or 3-(2-methyl-4-pyridyl)-5-cyano-4-isobutoxyphenyl)-1,2,4-triazole. In another embodiment, the xanthine oxidoreductase inhibitor includes 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, and pharmaceutically acceptable salts thereof. In a further embodiment, the xanthine oxidoreductase inhibitor is 2-[3-cyano-4-(2-methylpropoxy)phenyl]-4-methylthiazole-5-carboxylic acid and pharmaceutically acceptable salts thereof.

The phrase "pharmaceutically acceptable salt(s)", as used herein, means those salts of compounds of the invention that are safe and effective for administration to a patient and that do not adversely affect the therapeutic qualities of the compound. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., *J. Pharm. Sci.*, 1977; 66:1-19, incorporated herein by reference, in its entirety.

One of skill in the art will also understand that the xanthine oxidoreductase inhibitors incorporated into the methods of the current invention may also incorporate pharmaceutically acceptable excipients. The dosage forms of the present disclosure will typically include pharmaceutically acceptable excipients. As is well known to those skilled in the art, pharmaceutical excipients are routinely incorporated into solid dosage forms to alter the physical and chemical characteristics of the dosage form. This is done to ease the manufacturing process as well as to improve the performance of the dosage form. Common excipients include, but are not limited to diluents, bulking agents, lubricants, binders, preservatives, antioxidants, and combinations thereof.

As used herein, the term "hyperuricemia" denotes a disease state in which the patient has as an elevation in serum urate (sUA) levels greater than or equal to 6.0 mg/dL in women and men. Many factors contribute to hyperuricemia, including: genetics, insulin resistance, hypertension, renal insufficiency, obesity, diet, use of diuretics, and consumption of alcoholic beverages. Causes of hyperuricemia can be classified into three functional types: increased production of uric acid, decreased excretion of uric acid, and mixed type, incorporating both of the previous etiologies. Increased production etiologies result from high levels of purine in the diet and increased purine metabolism. Decreased excretion etiologies result from kidney disease, certain drugs, and competition for excretion between uric acid and other molecules. Mixed causes include high levels of alcohol and/or fructose in the diet, and starvation. Hyperuricemia typically develops into gout when urate crystals are formed from supersaturated body fluids and deposited in joints, tophi, and parenchymal organs due to a disorder in the urate metabolism. Uric acid is the end product of purine metabolism and is generated in the cascade of hypoxantine→xanthine→uric acid.

In addition to suffering from hyperuricemia and at least one second disease state, the patients being treated according to the methods of the present disclosure may also be suffering from at least one third (or more) additional disease states. These third or more additional disease states include, but are not limited to, gout, hypertension, chronic stable angina, renal failure, nephrolithiasis, acute gouty arthritis, chronic gouty joint disease, tophaceous gout, uric acid urolithiasis, uric acid nephropathy, progressive renal disease, and combinations thereof. Alternatively, the patients being treated according to the methods of the present invention may be suffering from both gout and hyperuricemia. In such instances, the patient will also be suffering from at least one third disease state. The patient is or will be concomitantly administered theophylline to treat the at least third disease state. The at least one third disease state includes, but is not limited to asthma, acute bronchitis, chronic bronchitis, emphysema, neonatal apnea, neonatal bradycardia and combinations theoreof. In addition, the patient may also be suffering from at least one fourth (or more) additional disease states. These fourth or more additional disease states include, but are not limited to, hypertension, chronic stable angina, renal failure, nephrolithiasis, acute gouty arthritis, chronic gouty joint disease, tophaceous gout, uric acid urolithiasis, uric acid nephropathy, progressive renal disease, and combinations thereof.

The methods of the current disclosure are directed to treating patients with secondary disease states that are indicated for, or require theophylline treatment. Theophylline is a methylxanthine compound used in the treatment of respiratory diseases resulting from airway constriction. Theophylline elicits a physiological response by two primary mechanisms, including competitive nonselective phosphodiesterase inhibitor, which raises intracellular cAMP, activates PKA, inhibits TNF-alpha and inhibits leukotriene synthesis, and reduces inflammation and innate immunity; and nonselective adenosine receptor antagonism, antagonizing A1, A2, and A3 receptors almost equally, which explains many of its cardiac effects and some of its anti-asthmatic effects. One skilled in the art will appreciate that the theophylline compound, as described herein is also known by its chemical name, 1,3-dimethyl-7H-purine-2,6-dione, its CAS Number, 58-55-9, and a multitude of brand name theophylline pharmaceutical products, incorporating theophylline as at least one of the active pharmaceutical ingredients. The theophylline component of the current methods also encompasses immediate release formulations, in addition to modified release formulations, including extended release, controlled release, and delayed release theophylline dosage forms. Dosage forms of theophylline may include tablets, capsules, sprinkle caps, liquid formulations, such as solutions and suspensions, and parenteral dosage forms including intravenous, intramuscular, intraarterial, intracerebral, intradermal, intrathecal, and intracerebral dosage forms, and subcutaneous dosage forms.

The methods of the current disclosure allow for theophylline to continue to be administered according to the manufacturer's suggested dosing of the compound. As used herein, the phrase "manufacturer's suggested dosing" signifies the dosing disclosed in the package insert of the theophylline dosage form and available in a variety of pharmaceutical treatment references. The methods of the current disclosure encompass the recommended dosing for all dosage forms, and include the treatment of all patients, for all disease states in which theophylline treatment may be effective. For example, a manufacturer's suggested dosing for oral theophylline may be 4-6 mg/kg. Thus, as described previously herein, in the present disclosure, administration of the theophylline is in an amount ranging from about 90% to about 110% of a manufacturer's recommended theophylline dosage amount in the absence of administration of at least one xanthine oxidoreductase inhibitor. If the manufacturer's suggested dosing is 4-6 mg/kg, about 90% to about 110% would be from about 3.6 to about 6.6 mg/kg.

The methods of the current disclosure are directed to treating hyperuricemia in patients having a secondary disease state that is indicated for, or is being treated with theophylline. The secondary disease states may include chronic obstructive pulmonary disease (COPD), chronic obstructive lung disease (COLD), chronic obstructive airway disease (COAD), chronic airflow limitation (CAL) and chronic obstructive respiratory disease (CORD), asthma, acute bronchitis, chronic bronchitis, emphysema, neonatal apnea, neonatal bradycardia, and combinations thereof. It is also contemplated that the patient requiring treatment for hyperuricemia may suffer from at least one additional disease state. Generally, the at least one additional disease state may be secondary to the patient's hyperuricemia, or may derive from an etiology unrelated to the hyperuricemia. Examples of the at least one additional disease state include, but are not limited to, gout, hypertension, renal failure, nephrolithiasis, acute gouty arthritis, chronic gouty arthritis, tophaceous gout, uric acid urolithiasis, uric acid nephropathy, progressive renal disease, and combinations thereof.

The methods of the current disclosure are based on the surprising findings that certain xanthine oxidoreductase inhibitors may be administered concomitantly with theophylline without adversely affecting blood serum levels and theophylline, and, consequently, avoiding the typical adjustment in dosing due to hyperuricemia treatment. Theophylline is metabolized by cytochrome P-450 (hereinafter "CYP 450") to 1-methylxanthine, 3-methylxanthine, and 1,3-methyluric acid. Further, metabolism of 1-methylxanthine to 1-methyluric acid is mediated by xanthine oxidase. The xanthine oxidoreductase inhibitors described herein are not expected to have any inhibitory effect on CYP 450 involved in the metabolism of theophylline; however, because the xanthine oxidoreductase inhibitors are non-purine selective inhibitors of xanthine oxidase, it is generally expected that the compounds affect the xanthine oxidase mediate metabolism of theophylline and will decrease the clearance of theophylline, leading to increased theophylline serum levels. As stated previously, theophylline has a narrow therapeutic window, and even small increases in blood serum levels of the compound may result in serious adverse effects for the patient. However, the inventors surprisingly found that the administration of the xanthine oxidoreductase inhibitors described herein do not adversely affect theophylline serum levels, and that adjustment of theophylline treatment dosages is not required. Additional details pertaining to the pharmacokinetic parameters of the coadministration of a xanthine oxidoreductase inhibitor and theophylline are described in the Examples.

Prior to the discovery of the present invention, in previous studies using the xanthine oxidoreductase inhibitor febuxostat, subjects taking concomitant therapy with certain medications, including theophylline, could be enrolled in the study only if the certain excluded medication was discontinued for a certain length of time. For example, as shown in Table 1 below, febuxostat study F-GT06-153 specifically provided that subjects taking theophylline could not be enrolled in the study, unless the theophylline was discontinued at least 30 days prior to the day 1 randomization visit.

TABLE 1

Inclusion Criteria for Febuxostat Study F-GT06-153

"5.2.4 Prohibited Concomitant Therapy
Subjects may not take any medication (other than study drug) for the purpose of lowering sUA levels. Subjects who have taken any of the excluded medications listed below, prior to the study, can be enrolled into the study if the excluded medication is discontinued at least 30 days prior to Day 1/Randomization Visit.
The following medications are not to be administered 30 days prior or during the study:
Any other urate-lowering drug, other than study drug;
Use of NSAIDs and COX-2 inhibitors other than protocol required prophylaxis therapy
(short-term use of NSAIDs and COX-2 inhibitors for treatment of gout flares is allowed);
Salicylates (chronic use of aspirin ≤325 mg/day is allowed);
Thiazide diuretics;
Losartan;
Azathioprine;
Mercaptopurine;
Theophylline;
IV Colchicine;
Cyclosporine;
Cyclophosphamide;
Pyrazinamide;
Sulfamethoxazole/trimethoprim;
Use of corticosteroids (chronic prednisone ≤10 mg/day or its equivalent and short-term use of higher doses of prednisone for treatment of gout flares is allowed);
Changes in hormone replacement therapy or oral contraceptive therapy within 3 months of the Day 1/Randomization Visit or during the course of the study."

As is evident from Table 1 above, the coadministration of theophylline and urate-lowering therapies is a significant clinical concern, and one that must be considered prior to initiation of urate-lowering therapies.

While hyperuricemia is one of the primary disease states treated by the xanthine oxidoreductase inhibitors discussed herein, one of skill in the art will appreciate that the methods of the current disclosure are equally applicable to other disease states that are typically treated by administration of one or more xanthine oxidoreductase inhibitors. These other disease states include, but are not limited to, gout, prostatitis, inflammatory bowel disease, QT interval prolongation, myocardial infarction, cardiac hypertrophy, hypertension, nephrolithiasis, renal impairment, chronic kidney disease, metabolic syndrome (also referred to as "Syndrome X" and includes, at least one of abdominal obesity, atherogenic dyslipidemia, insulin resistance, glucose intolerance, a prothrombotic state or a proinflammatory state), diabetes, diabetic nephropathy, congestive heart failure and combinations thereof (these conditions are sometimes collectively referred to herein as "at least one first disease state"). Accordingly, the current methods encompass treating a patient having one of the aforementioned at least one first disease state and also having a second disease state requiring theophylline treatment, through the administration of a xanthine oxidoreductase inhibitor without significant adjustment of the manufacturer's suggested dosing, and without inducing theophylline toxicity. Moreover, the current methods further encompass treating a patient having one of the aforementioned at least one first disease state, at least one second disease state requiring the theophylline treatment and at least one third disease state. In addition to suffering from hyperuricemia and at least one second disease state, the patients being treated according to the methods of the present disclosure may also be suffering from at least one third (or more) additional disease states. These third or more additional disease states include, but are not limited to, gout, hypertension, chronic stable angina, renal failure, nephrolithiasis, acute gouty arthritis, chronic gouty joint disease, tophaceous gout, uric acid urolithiasis, uric acid nephropathy, progressive renal disease, and combinations thereof.

By way of example, and not of limitation, examples of the present disclosure will now be given.

Example 1

Effects of Multiple Febuxostat Doses on the Pharmacokinetics of Theophylline Administration An experiment was performed to determine the effects of multiple doses of a xanthine oxidoreductase inhibitor, 2-[3-cyano-4-(2-methylpropoxy)phenyl]-4-methylthiazole-5-carboxylic acid, also known as "febuxostat", on theophylline doses. The experiment was a phase I, double-blind, randomized, 2-period crossover study, in which 24 patients (12 male and 12 female) were enrolled in the study. Specifically, the total duration of the study was approximately 8 weeks (60 days), consisting of a Screening Period (Days −28 to −2), Check-in (Day −1) for Period 1, 7-day Treatment, a Washout Period (minimum of 7 days), Check-in for Period 2, 7-day Treatment, Study Exit or Early Termination, and a Follow-up phone call 10±2 days after the last dose of study medication. Subjects received both Regimens A and B in randomly assigned order. These regimens consisted of 7 daily doses of double-blind febuxostat 80 mg (A: two encapsulated febuxostat 40 mg tablets or B: matching placebo) and one dose (on Day 5 of each period) open-label theophylline 400 mg tablet.

On Days 1 to 7 of each period, subjects received febuxostat 80 mg or matching placebo at approximately 0900 hours after a minimum 10-hour fast, and followed 1 hour later by a standardized breakfast. On Day 5 of each period, subjects received a single oral dose of Uniphyl® (theophylline, anhydrous) 400 mg tablet along with the daily dose of febuxostat or matching placebo; food was first allowed 4 hours postdose. Water was available as desired, except for 1 hour before through 1 hour after study drug administration. Only 240 mL of water was allowed during dosing. Subjects were discharged in the morning of Day 8 of each Period (1 and 2), after plasma and urine pharmacokinetic sample collections and all study procedures were completed. For Day −1 of Period 2, subjects returned to the clinic after a minimum of 7 day washout period. For all subjects that completed both Periods 1 and 2 (or discontinued the study prematurely at an Early Termination visit, i.e., withdrew from study), a follow-up phone call was made 10±2 days after the last dose of study medication or Early Termination (ET). The effect of multiple oral doses of febuxostat on the pharmacokinetics of a single oral dose of theophylline were evaluated through measurement of plasma and urine concentration levels of theophylline at designated time points. Safety, tolerability, and theophylline toxicity were assessed throughout the study by monitoring adverse effects, clinical laboratory tests, vital signs, ECGs, and physical examination findings.

Theophylline plasma concentrations were determined from 7 mL blood samples obtained according to the schedules in Table 1 below. Trough febuxostat plasma concentrations were determined from 6 mL blood samples obtained according to the schedules in Table 2.

TABLE 2

Period 1 and 2: Blood Collection Schedules for Determination of Plasma Concentrations of Theophylline and Febuxostat

| | Blood Sample Collection for Pharmacokinetics | |
|---|---|---|
| | Theophylline | Febuxostat |
| Day 5 of Periods 1 and 2 | Predose (up to 30 minutes prior to dosing [0 hour]) and at 1, 2, 3, 4, 6, 8, 10, 12, and 14 hours postdose | Predose (up to 30 minutes prior to dosing [0 hour]) |
| Day 6 of Periods 1 and 2 | 16, 24, and 32 hours post Day 5 dosing | Predose (up to 30 minutes prior to dosing [0 hour]) |
| Day 7 of Periods 1 and 2 | 40, 48, and 56 hours post Day 5 dosing | None |
| Day 8 of Periods 1 and 2 | 64 and 72 hours post Day 5 dosing | None |

Additionally, to ensure that the drug plasma levels were not altered buy secondary conditions and medications, this experiment required subjects to abstain from the use of certain medications and other agents prior to and during the testing periods. The excluded medications and agents are summarized in Table 3 (prescription and nonprescription), including specifications on applicable time points through completion of all study activities.

TABLE 3

Excluded Medications and Agents

| 6 weeks prior to Check-in (Day −1) | 28 days prior to Check-in (Day −1) | 14 days prior to Check-in (Day −1) | 48 hours prior to Check-in (Day −1) |
|---|---|---|---|
| Nicotine-containing products | Prescription medications | Foods or beverages containing grapefruit or Seville oranges | Alcohol-containing products |
| Hormonal contraception (oral, patch, implant, vaginal ring, or injectable) | Over-the-counter medications, vitamins, herbal, or dietary supplements | Food or beverages containing caffeine or xanthine related substances | |

TABLE 3-continued

Excluded Medications and Agents

| 6 weeks prior to Check-in (Day −1) | 28 days prior to Check-in (Day −1) | 14 days prior to Check-in (Day −1) | 48 hours prior to Check-in (Day −1) |
|---|---|---|---|
| Hormone replacement therapy | Hepatic or renal clearance altering agents (erythromycin, cimetidine, barbiturates, phenothiazines, etc) | Charbroiled foods | |
| Febuxostat or Allopurinol | | | |

Note:
excluded medications are from timepoints through completion of all study activities.

Subjects were instructed not to take any medications or non-prescription drugs, vitamins, herbal supplements, or dietary supplements within 28 days prior to Check-in (Day −1).

The subjects of the current experiment were administered the appropriate dosage regimens and the pharmacokinetic data were evaluated. Mean plasma theophylline concentration vs. time profiles (linear and log-linear formats) for the two treatment regimens are depicted in FIG. 1. Additionally, individual and summary statistics of noncompartmental pharmacokinetic parameter estimates for theophylline following coadministration with febuxostat or placebo are presented in Table 4 below.

eliminated with a mean terminal half-life of 9.69 hours following oral administration of 400 mg theophylline with placebo or febuxostat. Mean theophylline $C_{max}$ values were 4.14 and 4.39 µg/mL for subjects coadministered with placebo and febuxostat, respectively. Mean theophylline AUC(0-tlqc) values were 115 µg·r/mL and 122 µg·hr/mL for subjects coadministered with placebo and febuxostat, respectively. Likewise, mean AUC(0-inf) values were also comparable between regimens. The intersubject variability (% CV) of $C_{max}$ and AUC(0-tlqc) values of theophylline ranged from 29% to 40% and 44% to 45%, respectively. The estimated mean $T_{1/2}$,

TABLE 4

Summary of Theophylline Pharmacokinetic Parameter Estimates Following an Oral Dose of 400 mg Theophylline Coadministered With 80 mg Febuxostat or Matching Placebo

| | Tmax (hr) | Cmax (µg/mL) | AUC(0-tlqc) (µg · hr/mL) | AUC(0-inf)(a) (µg · hr/mL) | T½(a) (hr) | CL/F(a) (mL/h) | Vz/F(a) (mL) |
|---|---|---|---|---|---|---|---|
| Theophylline + Febuxostat (Regimen A) | | | | | | | |
| N | 23 | 23 | 23 | 18 | 18 | 18 | 18 |
| Mean | 8.43(b) | 4.39 | 122 | 114 | 9.69(c) | 4430 | 56900 |
| SD | 4.62 | 1.74 | 55.7 | 53.4 | 2.32 | 2370 | 20400 |
| CV % | 55 | 40 | 45 | 47 | 24 | 53 | 36 |
| Theophylline + Placebo (Regimen B) | | | | | | | |
| N | 23 | 23 | 23 | 18 | 18 | 18 | 18 |
| Mean | 7.05(b) | 4.14 | 115 | 107 | 9.69(c) | 4430 | 58200 |
| SD | 2.88 | 1.19 | 50.3 | 49.9 | 2.07 | 1930 | 17200 |
| CV % | 41 | 29 | 44 | 46 | 21 | 44 | 30 |

Regimen A: Febuxostat 80 mg (two 40 mg encapsulated tablets) QD for 7 consecutive days and a single oral dose of theophylline, anhydrous 400 mg tablet on Day 5.
Regimen B: Matching placebo for febuxostat 80 mg (two 40 mg encapsulated tablets) QD for 7 consecutive days and a single oral dose of theophylline, anhydrous 400 mg tablet on Day 5.
(a) The terminal phase of the pharmacokinetic profile of theophylline could not be adequately characterized in the remaining subjects.
(b) Median Tmax values for Regimens A and B were 6.02 and 6.00 hr, respectively.
(c) Harmonic mean T½ values for Regimens A and B were 9.13 and 9.28 hr, respectively.

As illustrated in Table 4 above, theophylline was absorbed with a mean $T_{max}$ value of 7 to 9 hours (median=6 hours) and CL/F, and $V_z/F$ values for theophylline were generally similar between the 2 treatment regimens.

TABLE 5

Summary of Total Amount of Theophylline and Its Metabolites Excreted in Urine Over 72 Hours Following an Oral Dose of 400 mg Theophylline Coadministered With 80 mg Febuxostat or Matching Placebo

| | Theophylline (mg) | 1,3-Dimethyluric acid (mg) | 1-Methyluric acid (mg) | 1-Methylxanthine (mg) | 3-Methylxanthine (mg) |
|---|---|---|---|---|---|
| Theophylline + Febuxostat (Regimen A) | | | | | |
| N | 23 | 23 | 23 | 23 | 23 |
| Mean | 35.0 | 105.2 | 3.1 | 40.1 | 26.9 |

TABLE 5-continued

Summary of Total Amount of Theophylline and Its Metabolites Excreted
in Urine Over 72 Hours Following an Oral Dose of 400 mg Theophylline
Coadministered With 80 mg Febuxostat or Matching Placebo

|      | Theophylline (mg) | 1,3-Dimethyluric acid (mg) | 1-Methyluric acid (mg) | 1-Methylxanthine (mg) | 3-Methylxanthine (mg) |
|------|------|------|------|------|------|
| SD   | 18.1 | 23.3 | 4.0  | 7.6  | 9.5  |
| CV % | 52   | 22   | 127  | 19   | 35   |
| | | Theophylline + Placebo (Regimen B) | | | |
| N    | 23   | 23   | 23   | 23   | 23   |
| Mean | 35.0 | 114.8| 56.2 | 0.1  | 30.9 |
| SD   | 16.8 | 32.2 | 17.4 | 0.4  | 11.6 |
| CV % | 48   | 28   | 31   | 337  | 38   |

Regimen A: Febuxostat 80 mg (two 40 mg encapsulated tablets) QD for 7 consecutive days and a single oral dose of theophylline, anhydrous 400 mg tablet on Day 5.
Regimen B: Matching placebo for febuxostat 80 mg (two 40 mg encapsulated tablets) QD for 7 consecutive days and a single oral dose of theophylline, anhydrous 400 mg tablet on Day 5.

As illustrated in Table 5 above, the mean amount of parent drug (i.e., theophylline) excreted in the urine over a 72 hour interval were comparable between regimen arms and consistent with the literature. See Melethil S et al., *Res Commun Chem Pathol Pharmacol.*, 1982; 35(2):341-4. The mean amounts of 1,3-dimethyluric acid and 3-methylxanthine were also similar between the 2 regimens. In contrast, 1-methyluric acid decreased and 1-methylxanthine increased in subjects administered theophylline with febuxostat compared with those subjects administered theophylline with placebo.

A statistical analysis of the data was also performed. The effects of sequence, period, and regimen on theophylline $T_{max}$, $\ln(C_{max})$, $\ln(AUC[0\text{-tlqc}])$, and $\ln(AUC[0\text{-inf}])$ following coadministration of febuxostat or placebo were assessed. None of the aforementioned effects were statistically significant on the pharmacokinetic parameters (P>0.05) observed in the experiment. Further, the bioavailability of theophylline coadministered with febuxostat (Regimen A) relative to that of theophylline with placebo (Regimen B) was assessed via point estimates and 90% confidence intervals for the ratios of the central values for $C_{max}$, AUC(0-tlqc), and AUC(0-inf), and is summarized in Table 6.

TABLE 6

Relative Bioavailability of Febuxostat Following Administration of a
Single Oral Dose of 80 mg Febuxostat

| Parameter | Point Estimate | 90% Confidence Interval |
|-----------|----------------|-------------------------|
| | Regimen A vs Regimen B | |
| Cmax       | 1.03 | (0.917, 1.149) |
| AUC(0-tlqc)| 1.04 | (0.927, 1.156) |
| AUC(0-inf) | 1.05 | (0.924, 1.189) |

Regimen A: Febuxostat 80 mg (two 40 mg encapsulated tablets) QD for 7 consecutive days and a single oral dose of theophylline, anhydrous 400 mg tablet on Day 5.
Regimen B: Matching Placebo for febuxostat 80 mg (two 40 mg encapsulated tablets) QD for 7 consecutive days and a single oral dose of theophylline, anhydrous 400 mg tablet on Day 5.
Note:
The point estimates and confidence intervals were obtained from the exponentiated results of analysis of the natural logarithm transformed data.

From the statistical analyses of the pharmacokinetic data, the point estimates for theophylline $C_{max}$, AUC(0-tlqc), and AUC(0-inf) were close to 100%, and the 90% confidence intervals for the ratios were within the bioequivalence limit of 0.80 to 1.25.

The results of this experiment showed that the maximum observed theophylline concentration (Cmax) and exposure to theophylline (AUC) were comparable between treatment with febuxostat and treatment with placebo. Therefore, no adjustment of the theophylline dose was needed when coadministered with febuxostat.

What is claimed is:

1. A method of treating hyperuricemia in a patient in need of treatment thereof, the method comprising the steps of:
administering to a patient suffering from hyperuricemia and at least one second disease state, a therapeutically effective amount of 2-[3-cyano-4-(2-methylpropoxy)phenyl]-4-methylthiazole-5-carboxylic acid or a pharmaceutically acceptable salt thereof, wherein the subject is also receiving concomitant administration of theophylline to treat the at least one second disease state, and further wherein (i) the administration of 2-[3-cyano-4-(2-methylpropoxy)phenyl]-4-methylthiazole-5-carboxylic acid or a pharmaceutically acceptable salt thereof, to the patient does not result in theophylline toxicity to the patient; and (ii) administration of the theophylline is in an amount ranging from about 90% to about 110% of a manufacturer's recommended theophylline dosage amount in the absence of administration of at least one xanthine oxidoreductase inhibitor.

2. The method of claim 1, wherein the second disease state is asthma.

3. The method of claim 1, wherein the patient is further suffering from at least one third disease state, wherein the third disease is gout.

4. The method of claim 1, wherein the theophylline dosage amount ranges from about 95% to about 105% of a manufacturer's recommended theophylline dosage amount in the absence of administration of at least one xanthine oxidoreductase inhibitor.

5. The method of claim 1, wherein the theophylline dosage amount ranges from about 99% to about 101% of a manufacturer's recommended theophylline dosage amount in the absence of administration of at least one xanthine oxidoreductase inhibitor.

6. The method of claim 1, wherein the patient suffering from hyperuricemia and the at least one second disease state is previously administered theophylline prior to initiation of treatment with 2-[3-cyano-4-(2-methylpropoxy)phenyl]-4-methylthiazole-5-carboxylic acid.

* * * * *